United States Patent
Gross et al.

(10) Patent No.: US 11,678,932 B2
(45) Date of Patent: Jun. 20, 2023

(54) ELECTRODE CATHETER WITH INCREMENTAL ADVANCEMENT

(71) Applicant: SYMAP MEDICAL (SUZHOU) LIMITED, Jiangsu (CN)

(72) Inventors: Yossi Gross, Moshav Mazor (IL); Yehuda Zadok, Holon (IL); Yaron Tal, Tel Mond (IL)

(73) Assignee: SYMAP MEDICAL (SUZHOU) LIMITED, Suzhou (CN)

( * ) Notice: Subject to any disclaimer, the term of this patent is extended or adjusted under 35 U.S.C. 154(b) by 1106 days.

(21) Appl. No.: 16/302,150

(22) PCT Filed: May 15, 2017

(86) PCT No.: PCT/IL2017/050533
§ 371 (c)(1),
(2) Date: Nov. 16, 2018

(87) PCT Pub. No.: WO2017/199240
PCT Pub. Date: Nov. 23, 2017

(65) Prior Publication Data
US 2020/0179044 A1    Jun. 11, 2020

Related U.S. Application Data

(60) Provisional application No. 62/338,115, filed on May 18, 2016.

(51) Int. Cl.
*A61B 18/14* (2006.01)
*A61B 18/00* (2006.01)

(52) U.S. Cl.
CPC .. *A61B 18/1492* (2013.01); *A61B 2018/0072* (2013.01); *A61B 2018/00404* (2013.01);
(Continued)

(58) Field of Classification Search
CPC ...... A61B 18/1492; A61B 2018/00404; A61B 2018/00434; A61B 2018/00511;
(Continued)

(56) References Cited

U.S. PATENT DOCUMENTS

| 4,106,488 A | 8/1978 | Gordon |
| 4,569,836 A | 2/1986 | Gordon |

(Continued)

FOREIGN PATENT DOCUMENTS

| CA | 2900160 | 8/2014 |
| CA | 2956945 | 2/2016 |

(Continued)

OTHER PUBLICATIONS

Buch E et al., "Intra-pericardial balloon retraction of the left atrium: A novel method to prevent esophageal injury during catheter ablation," Heart Rhythm 2008;5:1473-1475.
(Continued)

*Primary Examiner* — Michael F Peffley
*Assistant Examiner* — Bo Ouyang
(74) *Attorney, Agent, or Firm* — Law Offices of Albert Wai-Kit Chan, PLLC

(57) ABSTRACT

Apparatus comprises: (a) a longitudinal member (32), having a distal portion (34); (b) a plurality of electrodes (38) disposed on the distal portion of the longitudinal member, such that a first electrode (38*a*) of the plurality of electrodes is disposed distally along the longitudinal member from a second electrode (38*b*) of the plurality of electrodes; and (c) a controller (40). The controller comprises an actuator, and circuitry (42) electrically connected to the electrodes via the longitudinal member. The actuator is configured to move the longitudinal member in discrete incremental movements such that for each incremental movement, (i) before the incremental movement the first electrode is disposed in a
(Continued)

starting position, (ii) during each incremental movement the actuator moves second electrode toward the starting position, and (iii) at the end of each incremental movement the second electrode is stationary at the starting position.

10 Claims, 9 Drawing Sheets

(52) U.S. Cl.
CPC ............... *A61B 2018/00434* (2013.01); *A61B 2018/00511* (2013.01); *A61B 2018/00577* (2013.01); *A61B 2018/00732* (2013.01); *A61B 2018/1467* (2013.01); *A61B 2018/1497* (2013.01)

(58) Field of Classification Search
CPC .. A61B 2018/00577; A61B 2018/0072; A61B 2018/00732; A61B 2018/1467; A61B 2018/1497
See application file for complete search history.

(56) References Cited

U.S. PATENT DOCUMENTS

| | | | |
|---|---|---|---|
| 4,619,247 A | 10/1986 | Inoue | |
| 5,215,086 A | 6/1993 | Terry, Jr. et al. | |
| 5,251,634 A | 10/1993 | Weinberg | |
| 5,697,377 A | 12/1997 | Wittkampf | |
| 5,735,280 A | 4/1998 | Sherman et al. | |
| 5,776,063 A | 7/1998 | Dittrich et al. | |
| 5,807,285 A | 9/1998 | Vaitekunas | |
| 5,817,022 A | 10/1998 | Vesely | |
| 5,827,216 A | 10/1998 | Igo et al. | |
| 6,050,943 A | 4/2000 | Slayton | |
| 6,064,902 A | 5/2000 | Haissaguerre et al. | |
| 6,117,101 A | 9/2000 | Diederich | |
| 6,128,523 A | 10/2000 | Bechtold | |
| 6,161,048 A | 12/2000 | Sluijter | |
| 6,219,577 B1 | 4/2001 | Brown | |
| 6,233,477 B1 | 5/2001 | Chia | |
| 6,241,727 B1 | 6/2001 | Tu | |
| 6,246,899 B1 | 6/2001 | Chia | |
| 6,361,500 B1 | 3/2002 | Masters | |
| 6,405,732 B1 | 6/2002 | Edwards | |
| 6,425,877 B1 | 7/2002 | Edwards | |
| 6,440,077 B1 | 8/2002 | Jung | |
| 6,485,431 B1 | 11/2002 | Campbell | |
| 6,522,926 B1 | 2/2003 | Kieval | |
| 6,526,318 B1 | 2/2003 | Ansarinia | |
| 6,605,084 B2 | 8/2003 | Acker et al. | |
| 6,635,054 B2 | 10/2003 | Fjield et al. | |
| 6,641,579 B1 | 11/2003 | Bernardi | |
| 6,659,950 B2 | 12/2003 | Taheri | |
| 6,671,556 B2 | 12/2003 | Osorio et al. | |
| 6,684,105 B2 | 1/2004 | Cohen et al. | |
| 6,685,639 B1 | 2/2004 | Wang | |
| 6,692,490 B1 | 2/2004 | Edwards | |
| 6,701,931 B2 | 3/2004 | Sliwa et al. | |
| 6,736,835 B2 | 5/2004 | Pellegrino | |
| 6,740,040 B1 | 5/2004 | Mandrusov | |
| 6,805,129 B1 | 10/2004 | Pless et al. | |
| 6,845,267 B2 | 1/2005 | Harrison | |
| 7,001,336 B2 | 2/2006 | Mandrusov | |
| 7,022,105 B1 | 4/2006 | Edwards | |
| 7,037,306 B2 | 5/2006 | Podany et al. | |
| 7,149,574 B2 | 12/2006 | Yun | |
| 7,162,303 B2 | 1/2007 | Levin | |
| 7,226,440 B2 | 6/2007 | Gelfand et al. | |
| 7,311,701 B2 | 12/2007 | Gifford et al. | |
| 7,326,201 B2 | 2/2008 | Fjield et al. | |
| 7,430,449 B2 | 9/2008 | Aldrich | |
| 7,499,747 B2 | 3/2009 | Kieval | |
| 7,510,536 B2 | 3/2009 | Foley | |
| 7,553,284 B2 | 6/2009 | Vaitekunas | |
| 7,565,191 B2 | 7/2009 | Burbank et al. | |
| 7,608,072 B2 * | 10/2009 | Swanson | A61N 1/05 606/41 |
| 7,617,005 B2 | 11/2009 | Demarais | |
| 7,647,115 B2 | 1/2010 | Levin et al. | |
| 7,653,438 B2 | 1/2010 | Deem | |
| 7,662,099 B2 | 2/2010 | Podany et al. | |
| 7,684,865 B2 | 3/2010 | Aldrich | |
| 7,706,882 B2 | 4/2010 | Francischelli | |
| 7,717,948 B2 | 5/2010 | Demarais | |
| 7,787,946 B2 | 8/2010 | Stahmann et al. | |
| 7,840,271 B2 | 11/2010 | Kieval | |
| 7,853,333 B2 | 12/2010 | Demarais | |
| 7,854,733 B2 | 12/2010 | Govari | |
| 7,901,359 B2 | 3/2011 | Mandrusov | |
| 7,974,696 B1 | 7/2011 | DiLorenzo | |
| 8,197,409 B2 | 6/2012 | Foley | |
| 8,391,970 B2 | 3/2013 | Tracey et al. | |
| 8,585,601 B2 | 11/2013 | Sverdlik et al. | |
| 8,696,581 B2 | 4/2014 | Sverdlik et al. | |
| 8,702,619 B2 | 4/2014 | Wang | |
| 9,014,821 B2 | 4/2015 | Wang | |
| 9,028,417 B2 | 5/2015 | Sverdlik et al. | |
| 9,381,063 B2 | 7/2016 | Gang et al. | |
| 9,408,549 B2 | 8/2016 | Brockway et al. | |
| 9,439,598 B2 | 9/2016 | Shimada et al. | |
| 9,566,456 B2 | 2/2017 | Sverdlik et al. | |
| 9,770,593 B2 | 9/2017 | Gross | |
| 9,999,463 B2 | 6/2018 | Puryear et al. | |
| 10,004,557 B2 | 6/2018 | Gross | |
| 10,383,685 B2 | 8/2019 | Gross et al. | |
| 10,478,249 B2 | 11/2019 | Gross et al. | |
| 2001/0003798 A1 | 6/2001 | McGovern | |
| 2001/0007940 A1 | 7/2001 | Tu | |
| 2002/0091427 A1 | 7/2002 | Rappaport | |
| 2002/0147446 A1 | 10/2002 | Ein-Gal | |
| 2002/0173688 A1 | 11/2002 | Chen | |
| 2002/0193787 A1 | 12/2002 | Qin et al. | |
| 2003/0018256 A1 | 1/2003 | Sasaki | |
| 2003/0045909 A1 | 3/2003 | Gross et al. | |
| 2003/0055421 A1 | 3/2003 | West | |
| 2003/0069590 A1 | 4/2003 | Rabiner | |
| 2003/0013968 A1 | 6/2003 | Fjield | |
| 2004/0034339 A1 | 2/2004 | Stoller | |
| 2004/0038857 A1 | 2/2004 | Tracey | |
| 2004/0097788 A1 | 5/2004 | Mourlas | |
| 2004/0122494 A1 | 6/2004 | Eggers et al. | |
| 2004/0162507 A1 | 8/2004 | Govari et al. | |
| 2004/0162550 A1 | 8/2004 | Govari et al. | |
| 2004/0193021 A1 | 9/2004 | Savage | |
| 2005/0020921 A1 | 1/2005 | Glassell | |
| 2005/0080469 A1 | 4/2005 | Larson et al. | |
| 2005/0165298 A1 | 7/2005 | Larson | |
| 2005/0177209 A1 | 8/2005 | Leung et al. | |
| 2005/0192638 A1 | 9/2005 | Gelfand | |
| 2005/0203410 A1 | 9/2005 | Jenkins | |
| 2005/0222554 A1 | 10/2005 | Wallace et al. | |
| 2005/0251125 A1 | 11/2005 | Pless | |
| 2005/0288651 A1 | 12/2005 | Van Tassel et al. | |
| 2005/0288730 A1 | 12/2005 | Deem et al. | |
| 2006/0009753 A1 | 1/2006 | Fjield et al. | |
| 2006/0041277 A1 | 2/2006 | Deem | |
| 2006/0058711 A1 | 3/2006 | Harhen et al. | |
| 2006/0100514 A1 | 5/2006 | Lopath | |
| 2006/0184048 A1 | 8/2006 | Saadat | |
| 2006/0206150 A1 | 9/2006 | Demarais | |
| 2006/0212076 A1 | 9/2006 | Demarais | |
| 2006/0212078 A1 | 9/2006 | Demarais | |
| 2006/0241523 A1 | 10/2006 | Sinelnikov et al. | |
| 2006/0265014 A1 | 11/2006 | Demarais | |
| 2006/0265015 A1 | 11/2006 | Demarais | |
| 2006/0271111 A1 | 11/2006 | Demarais | |
| 2006/0276852 A1 | 12/2006 | Demarais | |
| 2006/0287648 A1 | 12/2006 | Schwartz | |
| 2007/0004984 A1 | 1/2007 | Crum et al. | |
| 2007/0021803 A1 | 1/2007 | Deem | |
| 2007/0038259 A1 | 2/2007 | Kieval | |
| 2007/0060972 A1 | 3/2007 | Kieval | |

(56) References Cited

U.S. PATENT DOCUMENTS

| | | |
|---|---|---|
| 2007/0093420 A1 | 4/2007 | Yeomans |
| 2007/0112327 A1 | 5/2007 | Lee |
| 2007/0129760 A1 | 6/2007 | Demarais |
| 2007/0129761 A1 | 6/2007 | Demarais |
| 2007/0133849 A1 | 6/2007 | Young et al. |
| 2007/0135875 A1 | 6/2007 | Demarais |
| 2007/0142879 A1 | 6/2007 | Greenberg |
| 2007/0167984 A1 | 6/2007 | Kieval |
| 2007/0162085 A1 | 7/2007 | DiLorenzo |
| 2007/0167913 A1 | 7/2007 | Elkins et al. |
| 2007/0173899 A1 | 7/2007 | Levin et al. |
| 2007/0191906 A1 | 8/2007 | Caparso |
| 2007/0203549 A1 | 8/2007 | Demarais |
| 2007/0239077 A1 | 10/2007 | Azhari et al. |
| 2007/0265610 A1 | 11/2007 | Thapliyal et al. |
| 2007/0265687 A1 | 11/2007 | Deem |
| 2007/0282407 A1 | 12/2007 | Demarais |
| 2008/0004614 A1 | 1/2008 | Burdette |
| 2008/0015445 A1 | 1/2008 | Saadat |
| 2008/0033415 A1 | 2/2008 | Rieker et al. |
| 2008/0039746 A1 | 2/2008 | Francischelli |
| 2008/0058682 A1 | 3/2008 | Azhari et al. |
| 2008/0058702 A1 | 3/2008 | Arndt |
| 2008/0071173 A1 | 3/2008 | Aldrich |
| 2008/0091109 A1 | 4/2008 | Abraham |
| 2008/0108984 A1 | 5/2008 | Burdette |
| 2008/0125819 A1 | 5/2008 | Ben-David et al. |
| 2008/0140180 A1 | 6/2008 | Dolan et al. |
| 2008/0172104 A1 | 7/2008 | Kieval |
| 2008/0183248 A1 | 7/2008 | Rezai |
| 2008/0215111 A1 | 9/2008 | Kieval |
| 2008/0255449 A1 | 10/2008 | Sinelnikov |
| 2008/0255642 A1 | 10/2008 | Zarins |
| 2008/0281379 A1 | 11/2008 | Wesselink |
| 2008/0288017 A1 | 11/2008 | Kieval |
| 2008/0288031 A1 | 11/2008 | Kieval |
| 2008/0306570 A1 | 12/2008 | Rezai |
| 2008/0312521 A1 | 12/2008 | Solomon |
| 2008/0319513 A1 | 12/2008 | Pu |
| 2009/0024195 A1 | 1/2009 | Rezai et al. |
| 2009/0048514 A1 | 2/2009 | Azhari |
| 2009/0062790 A1 | 3/2009 | Malchano |
| 2009/0062873 A1 | 3/2009 | Wu et al. |
| 2009/0076409 A1 | 3/2009 | Wu |
| 2009/0112133 A1 | 4/2009 | Deisseroth |
| 2009/0118780 A1 | 5/2009 | DiLorenzo |
| 2009/0137900 A1 | 5/2009 | Bonner et al. |
| 2009/0155336 A1 | 6/2009 | Rezai |
| 2009/0157068 A1* | 6/2009 | Kallel ............... A61B 18/1492 606/33 |
| 2009/0187230 A1 | 7/2009 | DiLorenzo |
| 2009/0192506 A9 | 7/2009 | Vaska et al. |
| 2009/0234407 A1 | 9/2009 | Hastings et al. |
| 2009/0247912 A1 | 10/2009 | Warnking |
| 2009/0270741 A1 | 10/2009 | Vanney et al. |
| 2009/0275827 A1 | 11/2009 | Aiken et al. |
| 2009/0287274 A1 | 11/2009 | Ridder |
| 2009/0326511 A1 | 12/2009 | Shivkumar |
| 2010/0004704 A1 | 1/2010 | Mazgalev |
| 2010/0010567 A1 | 1/2010 | Deem |
| 2010/0036292 A1 | 2/2010 | Darlington et al. |
| 2010/0042170 A1 | 2/2010 | Caparso |
| 2010/0105993 A1 | 4/2010 | Hassan |
| 2010/0113928 A1 | 5/2010 | Thapliyal |
| 2010/0130836 A1 | 5/2010 | Malchano |
| 2010/0137860 A1 | 6/2010 | Demarais |
| 2010/0137949 A1 | 6/2010 | Mazgalev |
| 2010/0137952 A1 | 6/2010 | Demarais et al. |
| 2010/0145428 A1 | 6/2010 | Cameron |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais |
| 2010/0191112 A1 | 7/2010 | Demarais |
| 2010/0204741 A1 | 8/2010 | Tweden |
| 2010/0217162 A1 | 8/2010 | Francischelli |
| 2010/0217369 A1 | 8/2010 | Gross |
| 2010/0222851 A1 | 9/2010 | Deem |
| 2010/0222854 A1 | 9/2010 | Demarais |
| 2010/0234728 A1 | 9/2010 | Foley |
| 2010/0256436 A1 | 10/2010 | Partsch |
| 2010/0268297 A1 | 10/2010 | Neisz |
| 2010/0305392 A1 | 12/2010 | Gross et al. |
| 2010/0312094 A1 | 12/2010 | Guttman et al. |
| 2011/0009734 A1 | 1/2011 | Foley |
| 2011/0015548 A1 | 1/2011 | Aldrich |
| 2011/0022133 A1 | 1/2011 | Bradford |
| 2011/0040171 A1 | 2/2011 | Foley |
| 2011/0040214 A1 | 2/2011 | Foley |
| 2011/0060324 A1 | 3/2011 | Wu |
| 2011/0092781 A1 | 4/2011 | Gertner |
| 2011/0092880 A1 | 4/2011 | Gertner |
| 2011/0112394 A1 | 5/2011 | Mishelevich |
| 2011/0112400 A1 | 5/2011 | Emery |
| 2011/0118598 A1 | 5/2011 | Gertner |
| 2011/0118600 A1 | 5/2011 | Gertner |
| 2011/0118725 A1 | 5/2011 | Mayse |
| 2011/0137149 A1 | 6/2011 | Gertner |
| 2011/0137298 A1 | 6/2011 | Chen |
| 2011/0172527 A1 | 6/2011 | Gertner |
| 2011/0172528 A1 | 6/2011 | Gertner |
| 2011/0172529 A1 | 6/2011 | Gertner |
| 2011/0178570 A1 | 6/2011 | Demarais |
| 2011/0184337 A1 | 6/2011 | Evans |
| 2011/0178541 A1 | 7/2011 | Azhari |
| 2011/0184322 A1 | 7/2011 | Brawer |
| 2011/0196248 A1 | 8/2011 | Grunwald |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2011/0251524 A1 | 10/2011 | Azhari |
| 2011/0257523 A1 | 10/2011 | Hastings et al. |
| 2011/0257564 A1 | 10/2011 | Demarais et al. |
| 2011/0257641 A1 | 10/2011 | Hastings et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0282203 A1 | 11/2011 | Tsoref |
| 2011/0282249 A1 | 11/2011 | Tsoref |
| 2011/0306851 A1* | 12/2011 | Wang ............... A61B 18/1492 600/301 |
| 2012/0029500 A1 | 2/2012 | Jenson |
| 2012/0029505 A1 | 2/2012 | Jenson |
| 2012/0029509 A1 | 2/2012 | Smith et al. |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0089047 A1 | 4/2012 | Ryba et al. |
| 2012/0095371 A1 | 4/2012 | Sverdlik et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0130363 A1 | 5/2012 | Kim |
| 2012/0150049 A1 | 6/2012 | Zielinski et al. |
| 2012/0157992 A1 | 6/2012 | Smith et al. |
| 2012/0172680 A1 | 7/2012 | Gelfand et al. |
| 2012/0191079 A1 | 7/2012 | Moll et al. |
| 2012/0197198 A1 | 8/2012 | Demarais |
| 2012/0197243 A1 | 8/2012 | Sherman et al. |
| 2012/0265198 A1 | 10/2012 | Crow et al. |
| 2012/0265227 A1 | 10/2012 | Sverdlik et al. |
| 2012/0290024 A1 | 11/2012 | Zhang et al. |
| 2012/0296240 A1 | 11/2012 | Azhari |
| 2012/0296329 A1 | 11/2012 | Ng |
| 2013/0012866 A1 | 1/2013 | Deem |
| 2013/0013024 A1 | 1/2013 | Levin |
| 2013/0085489 A1 | 4/2013 | Fain et al. |
| 2013/0103028 A1 | 4/2013 | Tsoref |
| 2013/0131743 A1 | 5/2013 | Yamasaki et al. |
| 2013/0165926 A1 | 6/2013 | Mathur |
| 2013/0204242 A1 | 8/2013 | Sverdlik et al. |
| 2013/0211396 A1 | 8/2013 | Sverdlik et al. |
| 2013/0211437 A1 | 8/2013 | Sverdlik et al. |

(56) References Cited

U.S. PATENT DOCUMENTS

| | | |
|---|---|---|
| 2013/0218029 A1 | 8/2013 | Cholette et al. |
| 2013/0218054 A1 | 8/2013 | Sverdlik et al. |
| 2013/0218068 A1 | 8/2013 | Sverdlik et al. |
| 2013/0231655 A1 | 9/2013 | Budzelaar et al. |
| 2013/0274614 A1 | 10/2013 | Shimada et al. |
| 2013/0274735 A1 | 10/2013 | Hastings et al. |
| 2013/0289369 A1 | 10/2013 | Margolis |
| 2013/0303876 A1 | 11/2013 | Gelfand et al. |
| 2013/0310674 A1 | 11/2013 | Deno et al. |
| 2013/0310823 A1 | 11/2013 | Gelfand et al. |
| 2013/0321262 A1* | 12/2013 | Schecter ............... A61B 34/76 345/156 |
| 2013/0322724 A1 | 12/2013 | Florent et al. |
| 2013/0324987 A1 | 12/2013 | Leung et al. |
| 2013/0324989 A1 | 12/2013 | Leung et al. |
| 2013/0331813 A1 | 12/2013 | Barbut et al. |
| 2014/0005706 A1 | 1/2014 | Gelfand et al. |
| 2014/0012133 A1 | 1/2014 | Sverdlik et al. |
| 2014/0018788 A1 | 1/2014 | Engelman et al. |
| 2014/0088561 A1 | 3/2014 | Levin et al. |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0243809 A1 | 8/2014 | Gelfand et al. |
| 2014/0257263 A1 | 9/2014 | Azamian et al. |
| 2014/0276036 A1 | 9/2014 | Collins et al. |
| 2014/0276063 A1 | 9/2014 | Park et al. |
| 2014/0276742 A1 | 9/2014 | Nabutovsky et al. |
| 2014/0288551 A1 | 9/2014 | Bharmi et al. |
| 2015/0011843 A1 | 1/2015 | Toth et al. |
| 2015/0045649 A1 | 2/2015 | O'Dea et al. |
| 2015/0073400 A1 | 3/2015 | Sverdlik et al. |
| 2015/0148601 A1 | 5/2015 | Weiner et al. |
| 2015/0164401 A1 | 6/2015 | Toth et al. |
| 2015/0173673 A1 | 6/2015 | Toth et al. |
| 2015/0216590 A1 | 8/2015 | Wang et al. |
| 2015/0224326 A1 | 8/2015 | Toth et al. |
| 2015/0245867 A1 | 9/2015 | Gross |
| 2015/0257779 A1 | 9/2015 | Sinelnikov et al. |
| 2015/0289929 A1 | 10/2015 | Toth et al. |
| 2015/0297113 A1 | 10/2015 | Kassab et al. |
| 2015/0297139 A1 | 10/2015 | Toth |
| 2016/0000499 A1 | 1/2016 | Lennox et al. |
| 2016/0106498 A1 | 4/2016 | Highsmith et al. |
| 2016/0113699 A1 | 4/2016 | Sverdlik et al. |
| 2016/0128767 A1 | 5/2016 | Azamian et al. |
| 2016/0324572 A1 | 11/2016 | Gross et al. |
| 2016/0338773 A1 | 11/2016 | Shimada et al. |
| 2017/0007157 A1 | 1/2017 | Gross et al. |
| 2017/0007158 A1 | 1/2017 | Gross et al. |
| 2017/0027460 A1 | 2/2017 | Shimada et al. |
| 2017/0035310 A1 | 2/2017 | Shimada et al. |
| 2017/0056104 A1 | 3/2017 | Asirvatham et al. |
| 2017/0172651 A1 | 6/2017 | Gross et al. |
| 2017/0215950 A1 | 8/2017 | Gross et al. |
| 2018/0168720 A1* | 6/2018 | Jensen ............... A61B 18/1492 |
| 2018/0221087 A1 | 8/2018 | Puryear et al. |
| 2018/0280082 A1 | 10/2018 | Puryear et al. |
| 2018/0303536 A1* | 10/2018 | Kafiluddi ............... A61B 18/02 |

FOREIGN PATENT DOCUMENTS

| | | |
|---|---|---|
| CN | 102551878 | 7/2012 |
| CN | 203089369 U | 7/2013 |
| EP | 2460486 | 6/2012 |
| WO | 1999/40957 | 8/1999 |
| WO | 03/097162 | 11/2003 |
| WO | 2006/072928 | 7/2006 |
| WO | 07/134258 | 11/2007 |
| WO | 2008/003058 | 1/2008 |
| WO | 2009/073208 | 6/2009 |
| WO | 2010/067360 | 6/2010 |
| WO | 2011/024159 | 3/2011 |
| WO | 2011/141918 | 11/2011 |
| WO | 2012/100211 | 7/2012 |
| WO | 2012/120495 | 9/2012 |
| WO | 2012/122157 | 9/2012 |
| WO | 2013/030738 | 3/2013 |
| WO | 2013/030743 | 3/2013 |
| WO | 2013/049601 | 4/2013 |
| WO | 2013/111136 | 8/2013 |
| WO | 2013/121424 | 8/2013 |
| WO | 2013/157009 | 10/2013 |
| WO | 2014/029355 | 2/2014 |
| WO | 2014/068577 | 5/2014 |
| WO | 2014/071223 | 5/2014 |
| WO | 2014/123512 | 8/2014 |
| WO | 2014/145853 | 10/2014 |
| WO | 2014/160832 | 10/2014 |
| WO | 2015/057696 | 4/2015 |
| WO | 2015/138225 | 9/2015 |
| WO | 2015/170281 | 11/2015 |
| WO | 2015/175948 | 11/2015 |
| WO | 2017/199240 | 11/2017 |

OTHER PUBLICATIONS

Cassak D, "Endosense: Facing technology and financing challenges in AF," IN-VIVO: The Business & Medicine Report, 36-44, Mar. 2010.

Di Biase L et al., "Prevention of phrenic nerve injury during epicardial ablation: Comparison of methods for separating the phrenic nerve from the epicardial surface," Heart Rhythm 2009;6:957-961.

Matsuo S et al., "Novel technique to prevent left phrenic nerve injury during epicardial catheter ablation," Circulation 2008;117:e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, Aug. Supplement 2009.

Sacher F et al "Phrenic Nerve Injury After Catheter Ablation of Atrial Fibrillation," Indian Pacing Electrophysiol J. Jan.-Mar. 2007; 7(1): 1-6.

A Restriction Requirement dated Feb. 25, 2013, which issued during the prosecution of U.S. Appl. No. 12/780,240.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

Tearney GJ et al., "Three-Dimensional coronary artery microscopy by intracoronary optical frequency domain imaging" JACC Cardiovasc Imaging. Nov. 2008; 1(6): 752-761.

An Office Action dated Aug. 21, 2015, which issued during the prosecution of U.S Appl. No. 13/771,853.

William E. Cohn, et al., "Contrast pericardiography facilitates intrapericardial navigation under fluoroscopy", Ann Thorac Surg 2010; 90: 1537-40. Accepted for publication Jun. 7, 2010.

Srijoy Mahapatra, et al., "Pressure frequency characteristics of the pericardial space and thorax during subxiphoid access for epicardial ventricular tachycardia ablation", Heart Rhythm 2010; 7:604-609.

Schuessler RB et al., "Animal studies of epicardial atrial ablation," Heart Rhythm, vol. 6, No. 12S, S41-S45, Dec. Supplement 2009.

An English translation of an Office Action dated Nov. 18, 2016, which issued during the prosecution of Chinese Patent Application No. 2013800692612.

An International Search Report and Written Opinion both dated Oct. 26, 2011, which issued during the prosecution of Applicant's PCT/IL11/00382.

An International Search Report and a Written Opinion both dated Sep. 17, 2012, which issued during the prosecution of Applicant's PCT/IL2012/000100.

An International Preliminary Report on Patentability dated Nov. 20, 2012, which issued during the prosecution of Applicant's PCT/IL11/00382.

An International Search Report dated Jul. 31, 2008, which issued during the prosecution of Applicant's PCT/US07/68818.

(56) References Cited

OTHER PUBLICATIONS

An Office Action dated Dec. 20, 2012, which issued during the prosecution of U.S. Appl. No. 11/653,115.
An Office Action dated Feb. 19, 2013, which issued during the prosecution of U.S. Appl. No. 13/010,555.
Fajardo et al., Effects of Hyperthermia in a Maligant Tumor, Cancer 45:613-623 (1980).
Short et al., Physical Hyperthermia and Cancer Therapy, Proceedings of the IEEE 68:133-142 (1980) p. 136 col. 2, para 6.
U.S. Appl. No. 60/370,190, filed Apr. 8, 2002.
U.S. Appl. No. 60/307,124, filed Jul. 23, 2001.
An Office Action dated May 17, 2013, which issued during the prosecution of U.S. Appl. No. 12/780,240.
An Invitation to pay additional fees dated Jun. 7, 2013, which issued during the prosecution of Applicant's PCT/IL2013/050134.
An International Search Report and a Written Opinion both dated Aug. 12, 2013 which issued during the prosecution of Applicant's PCT/IL2013/050134.
An International Search Report and a Written Opinion both dated Feb. 18, 2011 which issued during the prosecution of Applicant's PCT/IL2010/000683.
An International Preliminary Report of patentability dated Feb. 28, 2012 which issued during the prosecution of Applicant's PCT/IL2010/000683.
F. Mahfoud et al., Catherter-Based renal denervation increases insulin sensitivity and improves glucose metabolism. European Heart Journal 2010.
F. Mahfoud et al., Effects of Renal Sympathetic Denervation on Glucose Metabolism in Patients with Resistant Hypertension: A Pilot Study. Circulation 2011: 123 1940-1946.
Tai et al., Analysis of Nerve Conduction Including by Direct Current, J Comput Neuro. Published Online on 2009.
Ariav et al., Electrical Stimulation Induced Relaxation of Isolated Pig Aortas, Scientific Sessions 2011. American Heart Association. Abstract.
Stella et al., Cardiovascular Effects of Efferent renal nerve stimulation, Clin and Exper. Theory and Practice, 97-111, 1987.
Mortimer and Bhadra., Peripheral Nerve and Muscle Stimulation, Chapter 4.2, 1-48, 2004.
Stella et al., Effects of afferent renal nerve stimulation on renal hemodynamic and excretory functions, American Journal of physiology, 576-583, 1984.
Renal Sympathetic denervation in patients with treatment resistant hypertension, (1-7) Published online Nov. 2010.
Zhang et al., Mechanism of Nerve conduction Block induced by High-Frequency Biphasic Electrical Currents, IEEE Biomedical Engineering vol. 53 No. 12, 2006.
Bhadra et al., Reduction of the Onset Response in High-Frequency Nerve Block with Amplitude Ramps from Non-Zero Amplitudes, 650-653, 2009 IEEE.
Tai et al., Stimulation of Nerve Block by High-Frequency Sinusoidal Electrical Current Based on the Hodgkin-Huxley Model, IEEE Neural Systems and Rehabilitation engineering, vol. 13 No. 3, 2005.
Tsui, Electrical Nerve Stimulation, Springer Atlas of Ultrasound, pp. 9-18, 2008.
Bartus et al., Denervation (ablation) of Nerve Terminalis in renal arteries: early results of interventional treatment of arterial hypertension in Poland, Kardiologia Polska 2013, 71, 2: 152-158.
Krum et al., Catherter-Based Renal sympathetic denervation for resistant hypertension: A multicentre safety and proof-of-principle cohort study, Lancet 2009.
Chinushi M. et al., Blood pressure and autonomic responses to electrical stimulation of the renal arterial nerve before and after ablation of the renal artery, Pubmed, Hyper tension, Feb. 2013 61;(2) 450-6.
Wojakowski and Tendera, Renal sympathetic nerve in pathopysiology of resistant hypertension, European Society of Cardiology, downloaded on Jun. 2013.

Chinushi et al., Hemodynamic Responses and Histological Effects of Radiofrequency catheter Ablation to renal artery Sympathetic nerve. Abstract, downloaded on Jun. 2013.
Berjano, Biomedical Engineering Online Theoretical modeling for Radiofrequency Ablation: state-of-the-art and challenges for the future, published Apr. 2006.
Young and Henneman, Reversible block of nerve Conduction by Ultrasound, Archive of Neurology vol. 4, 1961.
Ballantine et al., Focal Destruction of nervous tissue by focused ultrasound : Biophysical factors influencing its Application, Medical Acoustics Research Group, 1956.
Colucci et al., Focused Ultrasound effects on nerve action potential in vitro, Department of Radiology, Harvard Medical Scholl, Ultrasound Med Biolog. 2009, 35(10); 1773-1747.
Damianou, MRI Monitoring of the effects of tissue interfaces in the penetration of high intensity focused ultrasound in kidney in vivo, Ultrasound in Med & Bilo., vol. 30 No. 9, 2004.
Daum et al., In vivo Demonstration of noninvasive thermal surgery of the liver and kidney using an ultrasonic phase array, Ultrasound in Med & Bilo., vol. 25 No. 7, 1087-1098, 1999.
Foley et al., Image guided HIFU Neurolysis of peripheral nerve to treat Spasticity and Pain, Ultrasound in Med & Bilo., vol. 30 No. 9, 1199-1207, 2004.
Foley et al., Image guided High-Intensity focused Ultrasound for Condition block of peripheral nerves, Biomed Engineering, vol. 35 No. 1, 2007.
Zhang and Solomon, Nerve Ablation by high Intensity focused Ultrasound (HIFU) in swine model: Investigating HIFU as a non invasive Nerve block tool, WCIO 2011. Abstract.
Hynynen et al., Noninvasive arterial occlusion using MRI-Guided focused Ultrasound, Ultrasound in Med & Bilo., vol. 22 No. 8, 1071-1077, 1996.
Iwamoto et al., focused Ultrasound for Tactile Felling display, ICAT 2001.
Lele, Effects of Ultrasonic radiation on peripheral Nerve, with Observation on local Hearting, Experimental Neurology 8, 47-83, 1963.
Miharn et al., Temporally-Specific modification of Myelinated Axon excitability in vitro following a single ultrasound pulse,Ultrasound in Med & Bilo., 1990.
Rubin et al., Acute effects of Ultrasound on skeletal muscle oxygen tension , blood flow and capillary density, Ultrasound in Med & Bilo., vol. 16 No. 3, 271*277, 1990.
Renal sympathetic nerve ablation for Uncontrolled Hypertension, The New England journal of medicine, 932-934, 2009.
Wu et al., Preliminary Experience using high Intensity focused Ultrasound for the treatment of patient with advanced stage renal malignancy. The Journal of Urology, vol. 170, 2237-2240, 2003.
Young and Henneman, Functional Effects of focused Ultrasound on Mammalian nerves, Science New Series, vol. 134, No. 3489, 1961, 1521-1522.
Mizelle et al., Role of Renal nerve in Compensatory adaptation to chronic reduction in sodium intake, American Physiological Society, 1987.
Gibson, The Present Status of Renal Sympathectomy, California and Western Medicine, vol. 45, No. 1, 1936.
Kassab et al., Renal Denervation Attenuates the Sodium Retention and Hypertension Associated With Obesity, Hypertension, 1995. Abstract.
Winternitz et al., Role of the Renal Sympathetic Nerves in the Development and Maintenance of Hypertension in the Spontaneously Hypertensive Rat, J. Clin Invest 66(5), 1980. Abstract.
Augustyniak et al., Sympathetic overactivity as a cause of hypertension in chronic renal failure, Hypertension vol. 20, Issue 1, 2002. Abstract.
Brief introduction to bioimpedance (from www.ucl.ac.uk-medphys-research-eit).
Fletcher, Effect of episodic hypoxia on sympathetic activity and blood pressure, Respyration Pysiology, vol. 119, issue 2-3, 2000. Abstract.
Fletcher et al., Blood pressure response to chronic episodic hypoxia: the renin-angiotensin system, Journal of Applied physiology, 2001.

(56) References Cited

OTHER PUBLICATIONS

Illis, Spinal Cord Synapses in the CAT: The Reaction of the Boutons Termineaux at the Motoneurone Surface to Experimental Denervation, Brain a Journal of Neurology, vol, 87 issue 3, 1963, First page only.
Kopelman et al., Upper dorsal thoracoscopic sympathectomy for palmar hyperhidrosis. The use of hamionic scalpel versus diathermy. Ann Chir Gynaecol. 2001:90(3):203-5. Abstract.
Hashmonai et al., Thoracoscopic sympathectomy for palmar hyperhidrosis, Surgical Endoscopy May 2001, vol. 15, Issue 5, pp. 435-441. Abstract.
Yoshimoto et al., Relationship between renal sympathetic nerve activity and renal blood flow during natural behavior in rats, American Journal of Physiology vol. 286, 2004.
DiBona. Dynamic Analysis of patterns of renal sympathetic nerve activity: Implications of renal functions, Exp Physiol. 90.2 pp. 159-161, 2004.
Valente et al., Laparoscopic renal denervation for intractable ADPKD-related pain, Nephrology Dialysis Transplantation vol. 6 issue 1, 2000.
An International Search Report and a Written Opinion both dated Aug. 11, 2015 which issued during the prosecution of Applicant's PCT/IB2015/053350.
An International Preliminary Report on Patentability dated Nov. 8, 2016, which issued during the prosecution of Applicant's PCT/IB2015/053350.
An Advisory Action dated Aug. 8, 2016, which issued during the prosecution of U.S. Appl. No. 13/771,853.
European Search Report dated Jun. 7, 2016, which issued during the prosecution of Applicant's European App No. 13850508.6.
U.S. Appl. No. 61/811,880, filed Apr. 15, 2013.
Schwarz et al;(2015) Autonomix presentation at TCT—Guidewire-Based Autonomic Neural Sensing From the Artery Lumen.
An International Search Report and a Written Opinion both dated Apr. 17, 2014 which issued during the prosecution of Applicant's PCT/IL2013/050903.
Luscher TF, Mahfoud F. Renal nerve ablation after symplicity htn-3: Confused at the higher level? Eur Heart J. 2014;35:1706-1711.
Lu (2015) Selective Proximal Renal Denervation Guided by Autonomic Responses Evoked via High-Frequency Stimulation in a Preclinical Canine Model.
Straub et al., 'A bacteria-induced switch of sympathetic effector mechanisms augments local inhibition of TNF-a and IL-6 secretion in the spleen' Jul. 2000 The FASEB Journal vol. 14 No. 10 1380-1388.
Gestel et al., 'Autonomic dysfunction in patients with chronic obstructive pulmonary disease (COPD)' J Thorac Dis 2010; 2:215-222.
Hering et al., 'Renal Denervation in Moderate to Severe CKD' J Am Soc Nephrol. [Jul. 2012]; 23(7): 1250-1257.
Jonson et al, 'Afferent electrical stimulation of mesenteric nerves inhibits duodenal HC03 secretion via a spinal reflex activation of the splanchnic nerves in the rat' [1988] Acta Physiologica Scandinavica, 133: 545-550. doi: 10.1111/j.1748-1716.1988.tb08439.x.
Jonson et al., 'Splanchnic nerve stimulation inhibits duodenal HC03-secretion in the rat' Am J Physiol. [Dec. 1988];255 (6 Pt 1):G709-12.
Schwan, H.P. And Kay, C.F., 1956. Specific resistance of body tissues.*Circulation Research*, 4(6), pp. 664-670.
Kees et al., 'Via beta-adrenoceptors, stimulation of extrasplenic sympathetic nerve fibers inhibits lipopolysaccharideinduced TNF secretion in perfused rat spleen' J Neuroimmunol. Dec. 2003;145(1-2):77-85.
pcta.org, 'New (Dec. 6, 2013) Medtronic Multi-Electrode Renal Denervation Device Gets CE Mark and Australian Approval' http://www.ptca.org/news/2013/1206_MEDTRONIC_SYMPLICITY.html.

BusinessWire, 'St. Jude Medical Receives European Approval for New Renal Denervation System That Reduces Total Ablation Time by More Than 80 Percent' (Aug. 29, 2013) 2013 European Society of Cardiology.
mananatomy.com, 'Duodenum' http://www.mananatomy.com/digestive-system/duodenum.
Rosas-Ballina et al., 'Splenic nerve is required for cholinergic anti-inflammatory pathway control of TNF in endotoxemia' Aug. 5, 2008, vol. 105, No. 31 www.pnas.org/cgi/doi10.1073/pnas.0803237105.
Krum, H., et al. "Device-based antihypertensive therapy: therapeutic modulation of the autonomic nervous system." Circulation 123.2 (2011): 209.
Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.
Bohm (2014) Symplicity HTN-3 trial_ what is it and what does it mean?.
Ruilope (2014) Was there real denervation in the Symplicity HTN-3 trial.
Esler (2010) Renal sympathetic denervation in patients with treatment-resistant hypertension (The Symplicity HTN-2 Trial).
Renal Catheterization—SymplicityTM Renal Denervation System—downloaded from medtronicrdn.com Jun. 26, 2013.
An Office Action dated Mar. 11, 2016, which issued during the prosecution of U.S. Appl. No. 13/771,853.
Persu A, Jin Y, Fadl Elmula FE, Jacobs L, Renkin J, Kjeldsen S. Renal denervation after symplicity htn-3: An update. Curr Hypertens Rep. 2014;16:460.
Renal denervation and symplicity htn-3: "Dubium sapientiae initium" (doubt is the beginning of wisdom). Circ Res. 2014;115:211-214.
Patel HC, Hayward C, Di Mario C. Symplicity htn 3: The death knell for renal denervation in hypertension? Glob Cardiol Sci Pract. 2014;2014:94-98.
An Office Action dated Jan. 8, 2015, which issued during the prosecution of U.S. Appl. No. 13/771,853.
An International Preliminary Report on Patentability dated Ma 5, 2015, which issued during the prosecution of Applicant's PCT/IL2013/050903.
U.S. Appl. No. 61/841,485, filed Jul. 1, 2013.
Changfeng (2009) Analysis of nerve conduction block induced by direct current.
Tsui (2008) Chapter 2 of Atlas of ultrasound and nerve stimulation guided regional anesthesia.
Changfeng (2005) Simulation of nerve block by high frequency sunusoidal electrical current.
Warchol-Celinska E, Januszewicz A, Prejbisz A, Kadziela J. Renal denervation after the symplicity htn-3 trial. Postepy Kardiol Interwencyjnej. 2014;10:75-77.
Calhoun DA, Jones D, Textor S, Goff DC, Murphy TP, Toto RD, White A, Cushman WC, White W, Sica D, Ferdinand K, Giles TD, Falkner B, Carey RM. Resistant hypertension: Diagnosis, evaluation, and treatment: A scientific statement from the American Heart Association professional education committee of the council for high blood pressure research Circulation. 2008.
Schlaich MP, Sobotka PA, Krum H, Whitbourn R, Walton A, Esler MD. Renal denervation as a therapeutic approach for hypertension: Novel implications for an old concept. Hypertension. 2009;54:1195-1201.
Esler MD, Bohm M, Sieved H, Rump CL, Schmieder RE, Krum H, Mahfoud F, Schlaich MP. Catheter-based renal denervation for treatment of patients with treatment-resistant hypertension: 36 month results from the Symplicity htn-2 randomized clinical trial. Eur Heart J. 2014;35:1752-1759.
U.S. Appl. No. 61/862,561, filed Aug. 6, 2013.
U.S. Appl. No. 61/722,293, filed Nov. 5, 2012.
"Blood pressure response to renal nerve stimulation in patients undergoing renal denervation: a feasibility study", Gal et al., Journal of Human Hypertension (2014), 1-4, Macmillan Publishers Limited.
Sarafidis PA, Bakris GL. Resistant hypertension: An overview of evaluation and treatment. J Am Coll Cardiol. 2008;52:1749-1757.

(56) References Cited

OTHER PUBLICATIONS

Mahfoud F, Cremers B, Janker J, Link B, Vonend O, Ukena C, Linz D, Schmieder R, Rump LC, Kindermann I, Sobotka PA, Krum H, Scheller B, Schlaich M, Laufs U, Bohm M. Renal hemodynamics and renal function after catheter-based renal sympathetic denervation in patients with resistant hypertension. Hypertension. 2012;60:419-424.
Kjeldsen SE, Fadl Elmula FE, Persu A, Jin Y, Staessen JA. Renal sympathetic denervation in the aftermath of symplicity htn-Blood Press. 2014;23:256-261.
Kandzari DE, Bhatt DL, Sobotka PA, O'Neill WW, Esler M, Flack JM, Katzen BT, Leon MB, Massaro JM, Negoita M, Oparil S, Rocha-Singh K, Straley C, Townsend RR, Bakris G. Catheter-based renal denervation for resistant hypertension: Rationale and design of the symplicity htn-3 trial. Clin Cardiol. 2012;35:528-535.
European Search Report dated May 9, 2017, which issued during the prosecution of Applicant's European App No. 16203956.4.
Krum H, Schlaich MP, Sobotka PA, Bohm M, Mahfoud F, Rocha-Singh K, Katholi R, Esler MD. Percutaneous renal denervation in patients with treatment-resistant hypertension: Final 3-year report of the symplicity htn-1 study. Lancet. 2014;383:622-629.
Esler M. Illusions of truths in the symplicity htn-3 trial: Generic design strengths but neuroscience failings. J Am Soc Hypertens. 2014;8:593-598.
Schmieder RE. Hypertension: How should data from symplicity htn-3 be interpreted? Nat Rev Cardiol. 2014;11:375-376.
Pathak A, Ewen S, Fajadet J, Honton B, Mahfoud F, Marco J, Schlaich M, Schmieder R, Tsioufis K, Ukena C, Zeller T. From symplicity htn-3 to the renal denervation global registry: Where do we stand and where should we go? Eurointervention. 2014;10:21-23.
Pokushalov, Evgeny, et al. "A randomized comparison of pulmonary vein isolation with versus without concomitant renal artery denervation in patients with refractory symptomatic atrial fibrillation and resistant hypertension." *Journal of the American College of Cardiology* 60.13 (2012): 1163-1170.
Ruilope, L.M. and Arribas, F., 2014. Resistant Hypertension and Renal Denervation. Considerations on the Results of the Symplicity HTN-3 Trial.*Reyista Española de Cardiología*, 67(11), pp. 881-882.
An Office Action dated Apr. 6, 2017, which issued during the prosecution of U.S. Appl. No. 13/771,853.
U.S. Appl. No. 61/989,741, filed May 7, 2014.
U.S. Appl. No. 62/158,139, filed May 7, 2015.
An Office Action dated Nov. 30, 2017, which issued during the prosecution of U.S. Appl. No. 14/794,737.
An Office Action dated Dec. 15, 2017, which issued during the prosecution of U.S. Appl. No. 14/795,529.
An International Search Report and a Written Opinion both dated Dec. 14, 2017, which issued during the prosecution of Applicant's PCT/IL2017/050967.
An International Search Report and a Written Opinion both dated Nov. 10, 2017, which issued during the prosecution of Applicant's PCT/IL2017/050533.
An Office Action dated Jan. 14, 2019, which issued during the prosecution of U.S. Appl. No. 14/972,756.
An International Search Report and a Written Opinion both dated May 24, 2017, which issued during the prosecution of Applicant's PCT/IL2017/050029.
An Invitation to pay additional fees dated Mar. 28, 2017, which issued during the prosecution of Applicant's PCT/IL2017/050029.
Notice of Allowance together with the English translation dated May 4, 2017 which issued during the prosecution of Chinese Patent Application No. 2013800692612.
An Office Action dated Jun. 15, 2017, which issued during the prosecution of U.S Appl. No. 14/440,431.
An Invitation to pay additional fees dated Sep. 11, 2017, which issued during the prosecution of Applicant's PCT/IL2017/050533.
Notice of Allowance dated Jan. 22, 2018, which issued during the prosecution of U.S. Appl. No/ 14/440,431.
Notice of Allowance dated May 25, 2018, which issued during the prosecution of U.S. Appl. No. 14/440,431.
Notice of Allowance dated Jun. 21, 2019, which issued during the prosecution of U.S. Appl. No. 15/147,081.
Notice of Allowance dated Mar. 15, 2019, which issued during the prosecution of U.S. Appl. No. 15/147,081.
An Advisory Action dated Apr. 18, 2019, which issued during the prosecution of U.S. Appl. No. 14/972,756.
An International Preliminary Report on Patentability dated Nov. 20, 2018, which issued during the prosecution of Applicant's PCT/IL2017/050533.
An Office Action dated May 15, 2018, which issued during the prosecution of U.S. Appl. No. 14/972,756.
An Office Action dated Jul. 19, 2018, which issued during the prosecution of U.S. Appl. No. 15/147,081.
An International Search Report and a Written Opinion both dated Jun. 11, 2018, which issued during the prosecution of Applicant's PCT/IL2018/050231.
Notice of Allowance dated Aug. 20, 2019, which issued during the prosecution of U.S. Appl. No. 15/330,790.
An Office Action dated Sep. 6, 2018, which issued during the prosecution of U.S. Appl. No. 15/001,615.
Notice of Allowance dated Aug. 19, 2019, which issued during the prosecution of U.S. Appl. No. 15/330,790.
An Office Action dated Feb. 21, 2019, which issued during the prosecution of U.S. Appl. No. 15/330,790.
Notice of Allowance dated May 24, 2019, which issued during the prosecution of U.S. Appl. No. 15/147,081.
U.S. Appl. No. 62/338,115, filed May 18, 2016.

\* cited by examiner

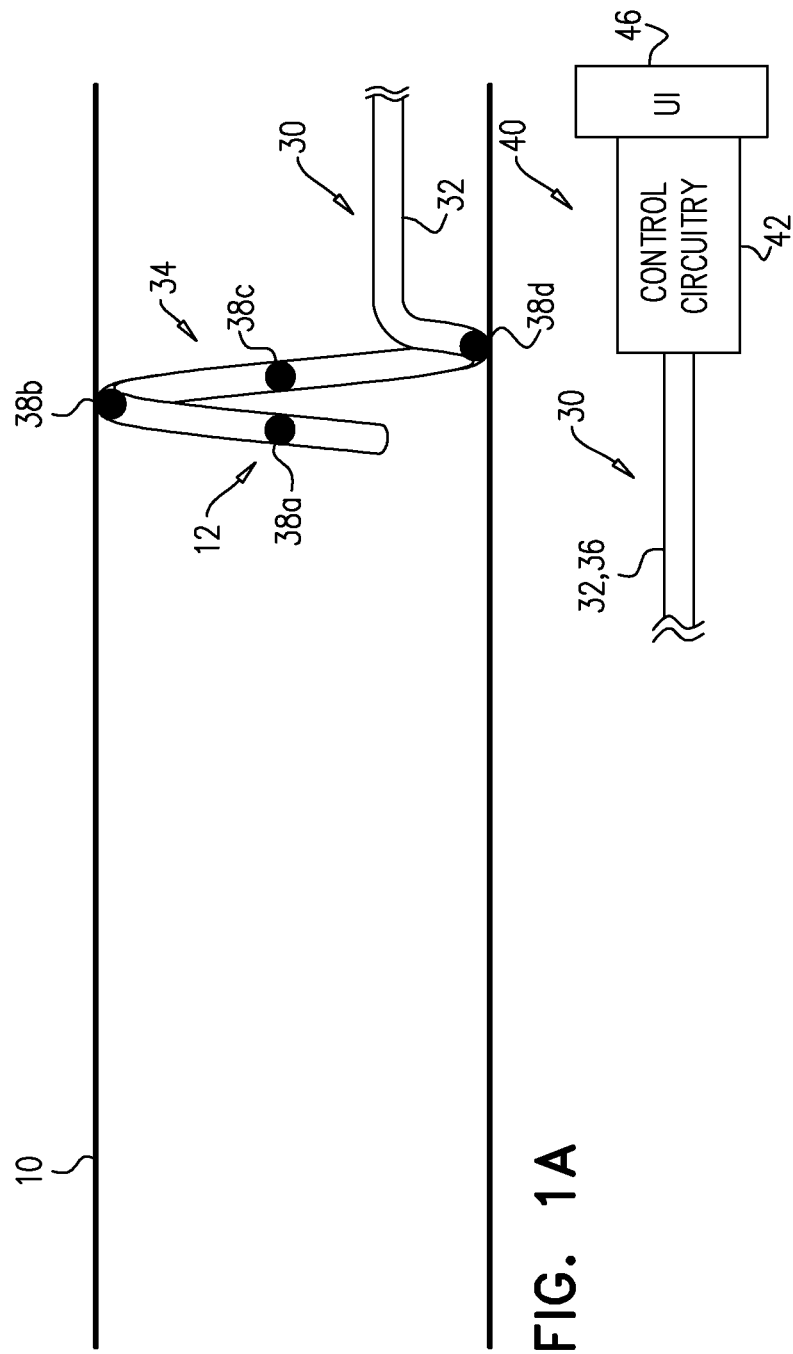

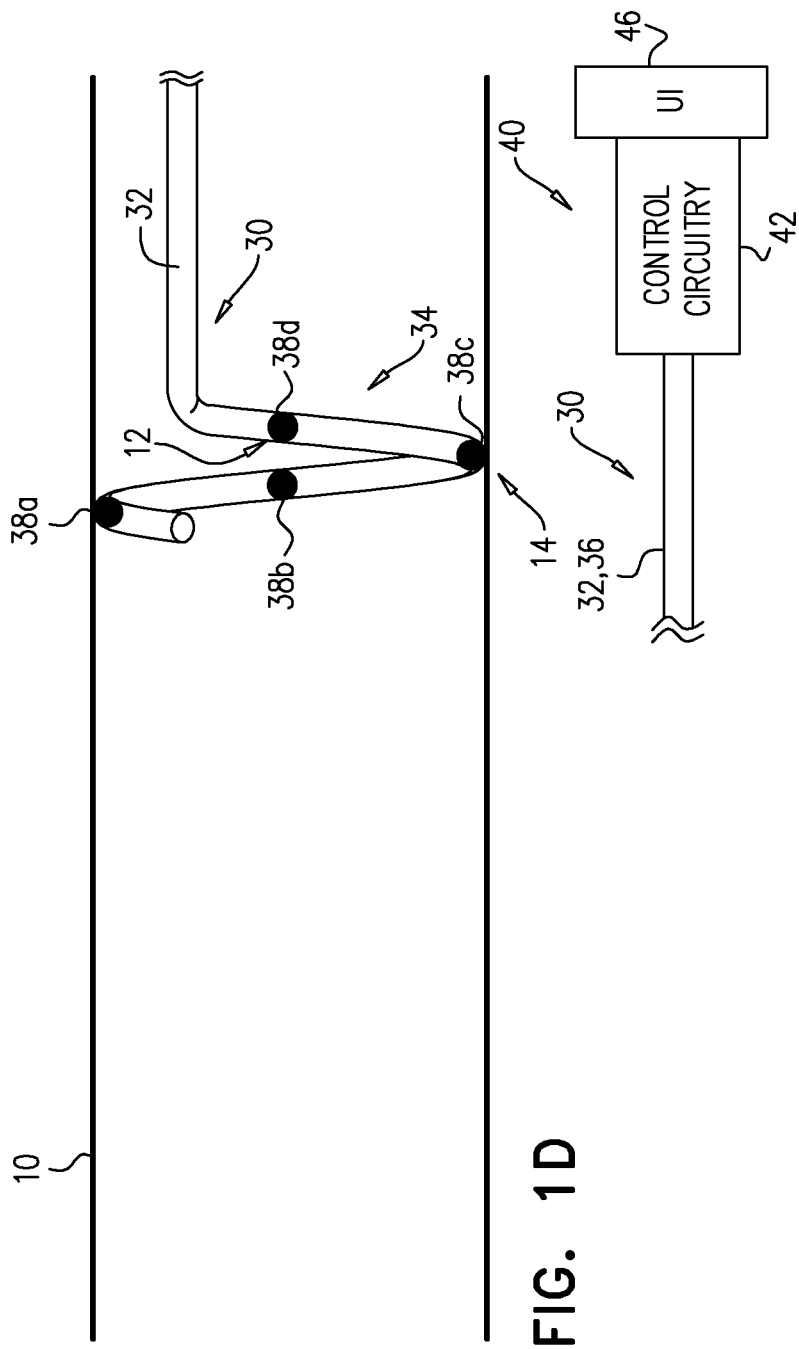

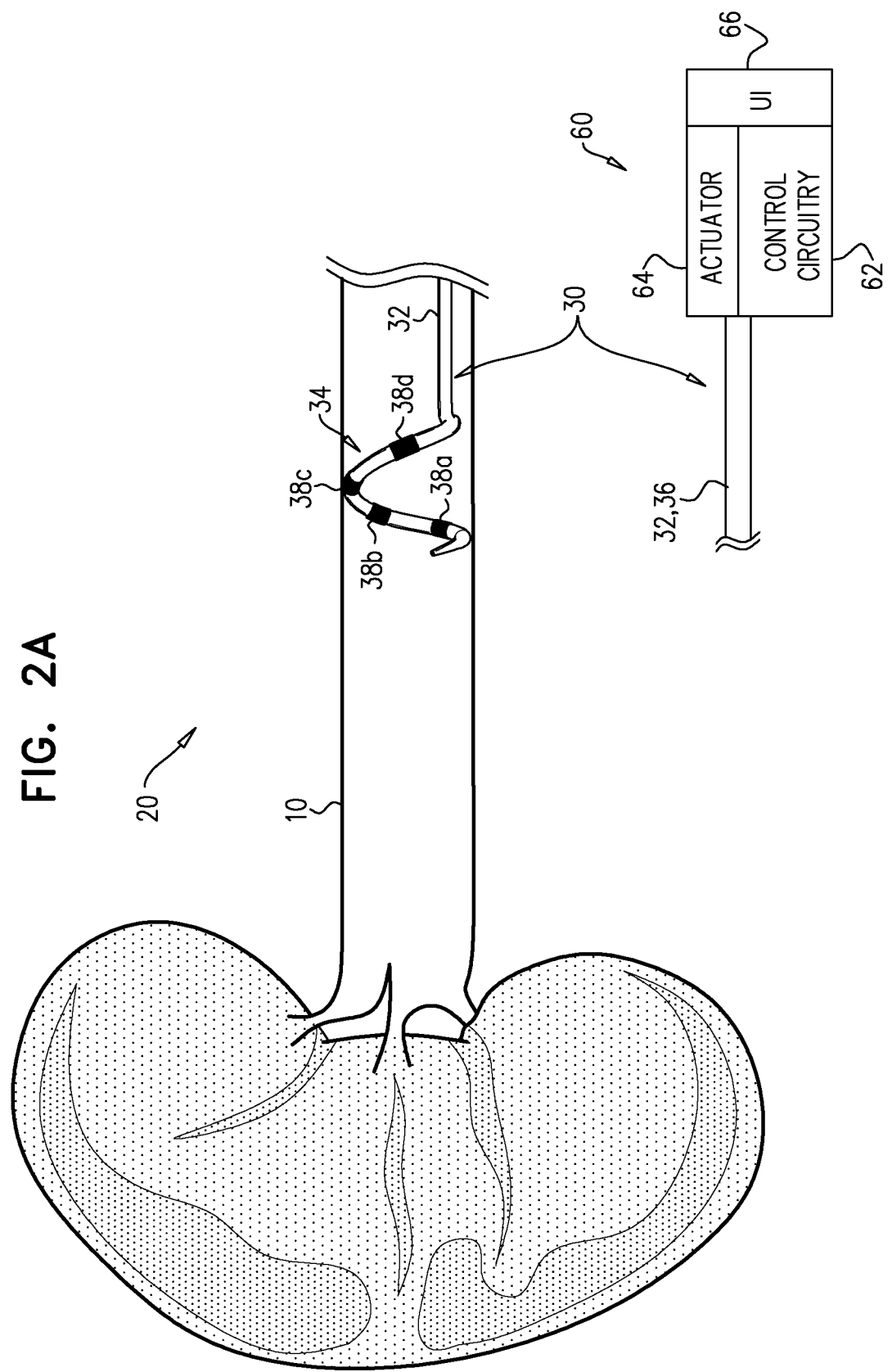

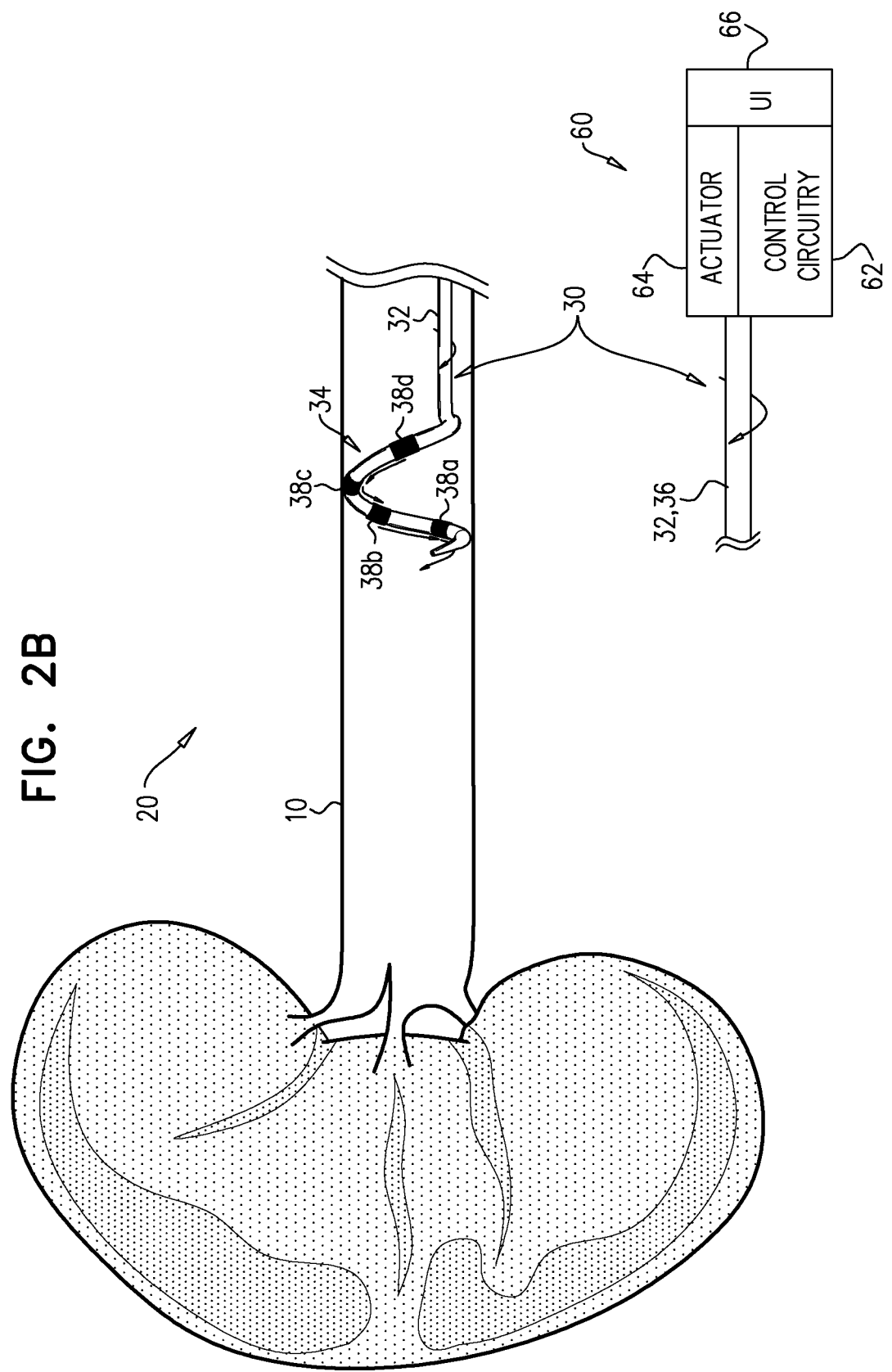

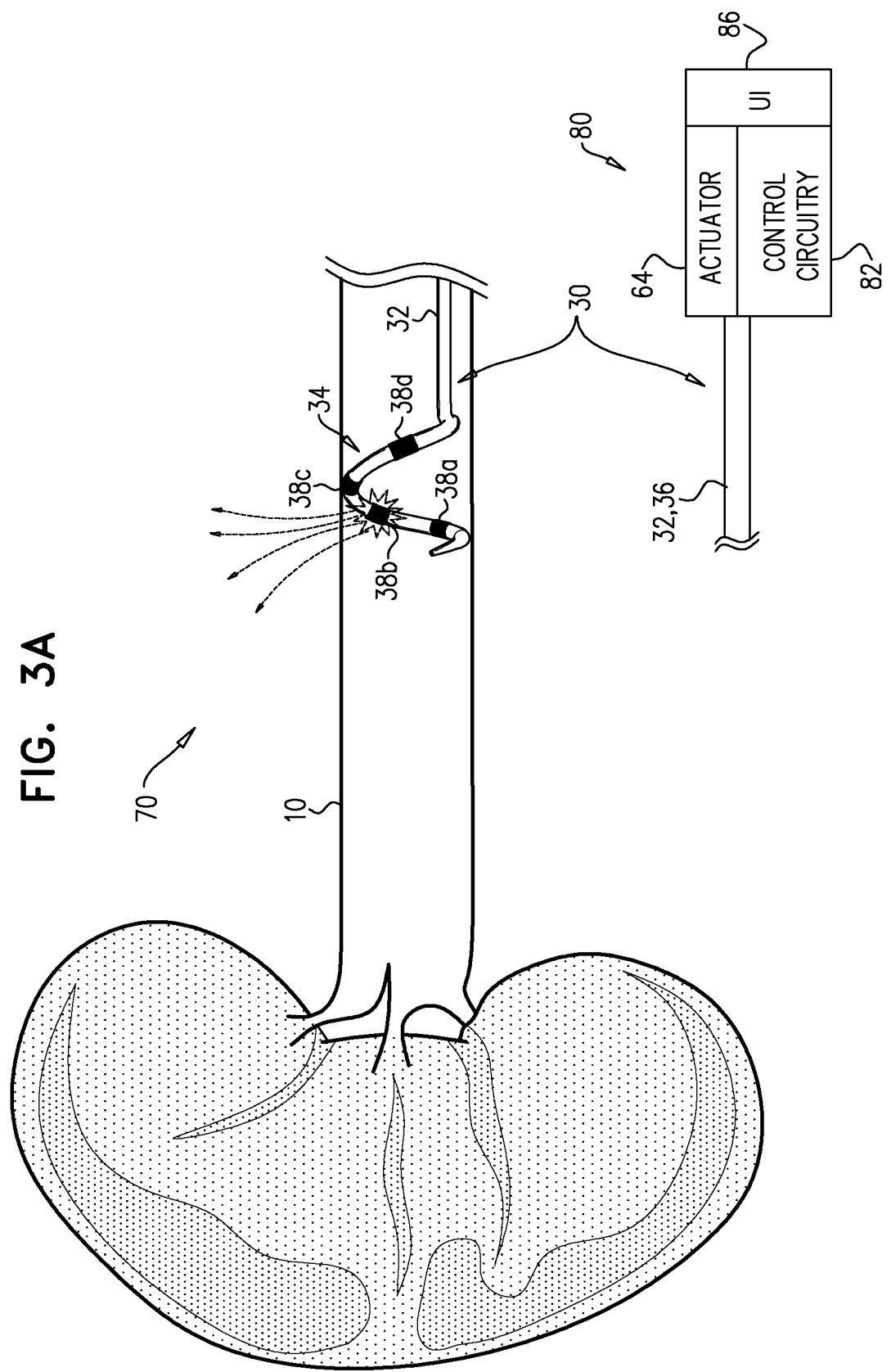

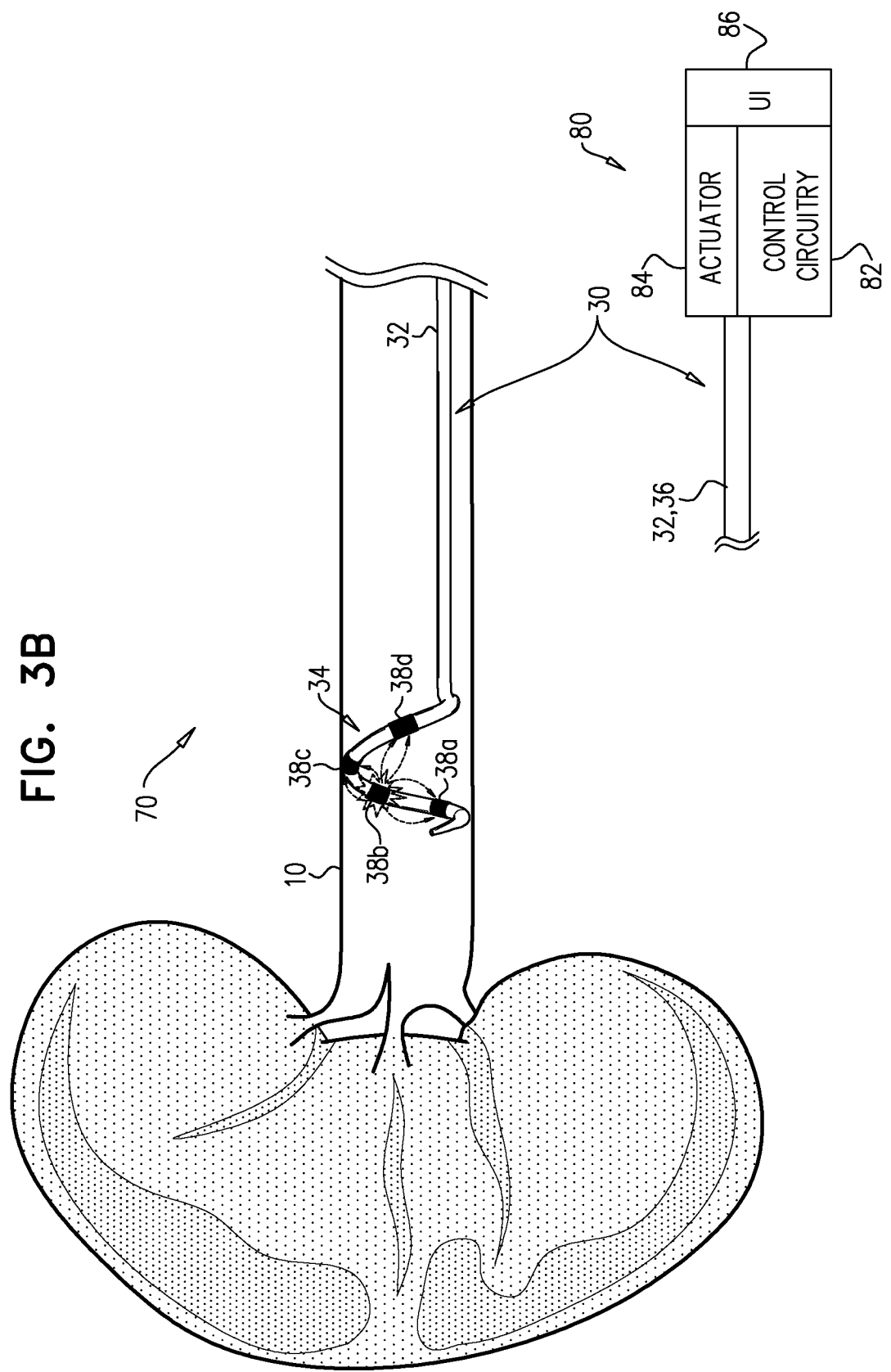

ELECTRODE CATHETER WITH INCREMENTAL ADVANCEMENT

CROSS-REFERENCES TO RELATED APPLICATIONS

The present application is the US National Phase of PCT application IL2017/050533 to Yossi GROSS et al., filed May 15, 2017, entitled "HELICAL CATHETER," which published as WO 2017/199240, and which claims priority to U.S. provisional patent application 62/338,115 to Yossi GROSS et al., filed May 18, 2016, and entitled "HELICAL CATHETER," which is incorporated herein by reference.

FIELD OF THE INVENTION

Applications of the present invention relate generally to ablation of tissue. Some applications of the present invention relate more specifically to ablation of tissue of the renal artery.

BACKGROUND

Hypertension is a prevalent condition in the general population, particularly in older individuals. Sympathetic nervous pathways, such as those involving the renal nerve, are known to play a role in regulating blood pressure. Ablation of renal nerve tissue from the renal artery is a known technique for treating hypertension.

SUMMARY OF THE INVENTION

Apparatus and methods are provided for improving nerve ablation procedures, including inter alia by reducing the number of steps, the number of movements, and/or the amount of time required. The apparatus and methods may be particularly useful for renal nerve ablation procedures. For some applications, ablative current is applied by one electrode and excitatory current is applied by another electrode, without it being necessary to move the electrodes. The electrodes are then moved in a stepwise procession through the artery with which the nerve is associated.

Also described are techniques for applying current to the wall of an artery in a manner that emulates monopolar current application, but without the use of a skin-based return electrode.

There is therefore provided, in accordance with an application of the present invention, a method, including:

advancing into a blood vessel of a subject a distal portion of a longitudinal member having a plurality of electrodes disposed thereon, such that a first electrode of the plurality of electrodes is disposed at a starting position, the first electrode being disposed, along the distal portion, distally to a second electrode of the plurality of electrodes;

using a controller to drive the first electrode to apply an ablative current;

using the controller to drive the second electrode to apply an excitatory current; and subsequently, moving the longitudinal member distally such that the second electrode moves toward the starting position of the first electrode, and stops at the starting position of the first electrode.

In an application, the distal portion of the longitudinal member has an operational shape in which it is curved to define a helix, the plurality of electrodes are distributed in a helical arrangement along the distal portion of the longitudinal member, and the step of moving the longitudinal member distally includes moving the longitudinal member distally and rotating at least the distal portion of the longitudinal member such that the second electrode moves toward the starting position of the first electrode, and stops at the starting position of the first electrode.

In an application, the method further includes, subsequently to the step of moving the longitudinal member:

using the controller to drive the first electrode to apply an ablative current to tissue distal to the starting position of the first electrode; and using the controller to drive the second electrode to apply an excitatory current to tissue at the starting position of the first electrode.

There is further provided, in accordance with an application of the present invention, apparatus for use with a blood vessel of a subject, the apparatus including:

a longitudinal member, having a distal portion that is transluminally advanceable into the blood vessel;

a plurality of electrodes disposed on the distal portion of the longitudinal member, such that a first electrode of the plurality of electrodes is disposed distally along the longitudinal member from a second electrode of the plurality of electrodes; and a controller, including:

circuitry electrically connected to the electrodes via the longitudinal member, and an actuator, mechanically connected to the longitudinal member, and configured to move the longitudinal member in discrete incremental movements such that for each incremental movement, (a) before the incremental movement the first electrode is disposed in a starting position, (b) during each incremental movement the actuator moves second electrode toward the starting position of the first electrode, and (c) at the end of each incremental movement the second electrode is stationary at the starting position of the first electrode.

In an application:

the plurality of electrodes includes a third electrode and a fourth electrode, the third electrode is disposed distally along the longitudinal member from the fourth electrode, and the actuator is configured to move the longitudinal member in incremental movements such that for each incremental movement, (a) before the incremental movement the third electrode is disposed in a starting position, (b) during each incremental movement the actuator moves fourth electrode toward the starting position of the third electrode, and (c) at the end of each incremental movement the fourth electrode is stationary at the starting position of the third electrode.

In an application:

the plurality of electrodes includes a third electrode and a fourth electrode, the third electrode is disposed distally along the longitudinal member from the fourth electrode, and the actuator is configured to move the longitudinal member in incremental movements such that for each incremental movement, (a) before the incremental movement the third electrode is disposed in a starting position, (b) during each incremental movement the actuator moves fourth electrode toward the starting position of the third electrode, and (c) at the end of each incremental movement the fourth electrode is stationary at the starting position of the third electrode, wherein the circuitry is configured to, after each incremental movement, drive the first and third electrodes to apply ablative current, and to drive the second and fourth electrodes to apply excitatory current.

In an application, the distal portion of the longitudinal member has an operational shape in which it is curved to define a helix, the plurality of electrodes is distributed in a helical arrangement along the distal portion of the longitudinal member, and the actuator is configured to move the second electrode into the starting position of the first electrode by advancing and rotating the longitudinal member.

In an application, the actuator includes a servomotor.

In an application, the circuitry is configured to drive the first electrode to apply ablative current, and to drive the second electrode to apply excitatory current.

In an application, the circuitry is configured to drive the first electrode to apply ablative current, and to drive the second electrode to apply excitatory current after each incremental movement.

In an application, the circuitry is configured to configure the ablative current to have a frequency of 450-550 kHz.

In an application, the circuitry is configured to configure the excitatory current to have a frequency of 20-500 Hz.

In an application, the circuitry is configured to drive the first electrode to apply the ablative current independently from driving the excitatory current.

There is further provided, in accordance with an application of the present invention, apparatus for use with a blood vessel of a subject, the apparatus including:
- a longitudinal member, having a distal portion that is transluminally advanceable into the blood vessel;
- a plurality of electrodes disposed on the distal portion of the longitudinal member; and
- a controller, including circuitry electrically connected to the electrodes via the longitudinal member, and having:
  - a first state in which the controller drives one of the electrodes to apply ablative current, and configures the other electrodes not to serve as return electrodes for the ablative current, and
  - a second state in which the controller drives one of the electrodes to apply ablative current, and configures more than one of the other electrodes to serve as return electrodes for the ablative current.

In an application, the distal portion of the longitudinal member has an operational shape in which it is curved to define a helix, and the plurality of electrodes are distributed in a helical arrangement along the distal portion of the longitudinal member.

In an application, the controller has a third state in which the controller drives one of the electrodes to apply ablative current, and configures more than one of the other electrodes to serve as return electrodes for the ablative current, wherein one of the electrodes that serves as a return electrode in the third state is the electrode that in the second state the controller drives to apply ablative current.

In an application, the electrode that in the first state the controller drives to apply ablative current is the same electrode as the electrode that in the second state the controller drives to apply ablative current.

In an application, the controller has another state in which the controller drives one of the electrodes to apply ablative current, and configures only one of the other electrodes to serve as a return electrode for the ablative current.

In an application, in the first state, the controller is configured to configure the ablative current to have a frequency of 450-550 kHz, and a power of 1-7 W.

The present invention will be more fully understood from the following detailed description of applications thereof, taken together with the drawings, in which:

BRIEF DESCRIPTION OF THE DRAWINGS

FIGS. 1A, 1B, 1C, and 1D are schematic illustrations of a method for use with a blood vessel of a subject, in accordance with some applications of the invention;

FIGS. 2A and 2B are schematic illustrations of a system for use with a blood vessel of a subject, in accordance with some applications of the invention; and FIGS. 3A, 3B, and 3C are schematic illustrations of a system for use with a blood vessel of a subject, in accordance with some applications of the invention.

DETAILED DESCRIPTION OF EMBODIMENTS

Figure 1B:
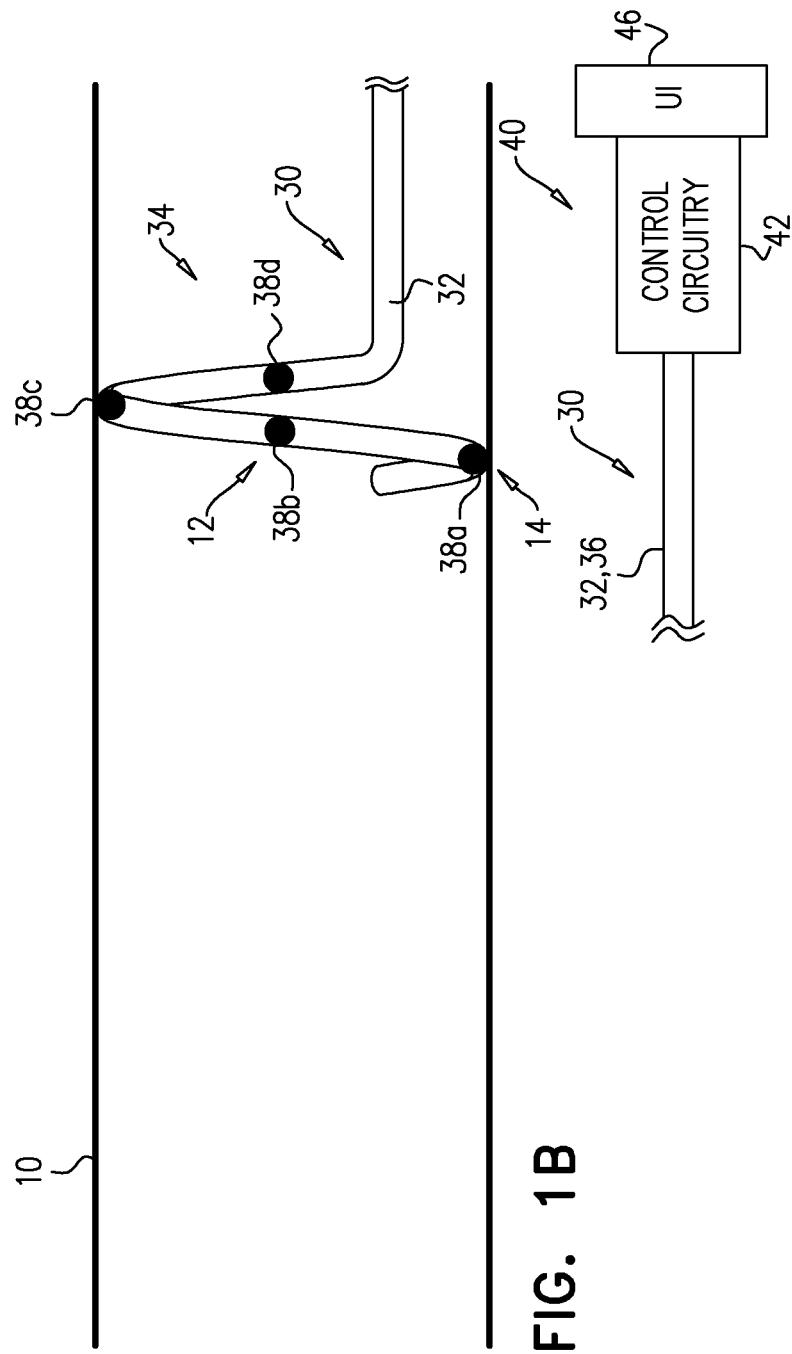

It is possible to use an excitatory current (i.e., a current configured to induce action potentials in nerve tissue) in order to locate renal nerves, and to monitor the progress of ablation of these nerves. Changes in one or more physiological parameters of the subject in response to the excitatory current indicate that the electrode used to apply the excitatory current is in proximity to a renal nerve, and that renal nerve is still at least partly functioning. Such parameters are typically related to blood pressure and/or heart rate. Techniques for locating and/or monitoring ablation of renal nerves (and other nerves) are described in the following patent applications, which are incorporated herein by reference:

PCT application publication WO 2014/068577 to Gross et al., filed Nov. 3, 2013, and entitled "Controlled tissue ablation,"

PCT application publication WO 2015/170281 to Gross et al., filed May 7, 2015, and entitled "Controlled tissue ablation techniques,"

U.S. patent application Ser. No. 14/794,737 to Gross et al., filed Jul. 8, 2015, and entitled "Electrical signal-based electrode-tissue contact Detection," which published as US 2017/0007157, U.S. patent application Ser. No. 14/972,756 to Gross et al., filed Dec. 17, 2015, and entitled "Transluminal electrode catheters, which published as US 2017/0172651"

U.S. patent application Ser. No. 15/001,615 to Gross et al., filed Jan. 20, 2016, and entitled "Catheter guidance and procedure planning, which published as US 2017/0202614" and U.S. patent application Ser. No. 15/147,081 to Gross et al., filed May 5, 2016 and entitled "Techniques for use with nerve tissue," which published as US 2016/0324572.

Such techniques may be time-consuming, e.g., because multiple excitations and/or ablations are typically required, because frequent repositioning of the electrode catheter is typically required, and because it is typically necessary to allow the parameter(s) being measured to return to baseline before the next application of current.

Reference is made to FIGS. 1A-D, which are schematic illustrations of a method for use with a blood vessel (e.g., a renal artery) 10 of a subject, in accordance with some applications of the invention. The method is hypothesized to reduce the number of steps required for a nerve-locating and/or nerve-ablating procedure by facilitating the application of ablative and excitatory current to artery 10 without movement of the electrode catheter. The method involves iteratively moving an electrode (e.g., an excitatory electrode) into the position within artery 10 that another electrode previously occupied.

An electrode catheter 30 comprises a longitudinal member 32, which has a distal portion 34 that is transluminally advanceable into blood vessel 10, and a proximal portion 36. Catheter 30 further comprises a plurality of electrodes 38 (e.g., a first electrode 38a, a second electrode 38b, a third electrode 38c, and a fourth electrode 38d) disposed on distal portion 34, typically distributed along member 32. For example, electrode 38a is disposed distally along longitudinal member 32 from electrode 38b. For example, along distal portion 34, electrode 38a is disposed distally to electrode 38b, which is disposed distally to electrode 38c, which is disposed distally to electrode 38d.

It is to be noted that, although catheter 30 is shown having four electrodes, for some applications the catheter comprises a different number of electrodes, such as two, three, five, six, seven, eight, or more. Similarly, although the helical shape of distal portion 34 is shown as having one helical turn, it may have more than one helical turn. Catheter 30 may in fact have more than one helical turn with more than four electrodes arranged in more than one helical turn along distal portion 34.

Distal portion 34 of longitudinal member 32 is advanced into blood vessel 10, such that a first electrode 38a of the plurality of electrodes is disposed at a starting position 12 of that electrode (FIG. 1A). (It is to be noted that the term "starting position" (including in the specification and in the claims) does not necessarily mean the first position in which the electrode is disposed after entering artery 10.) A controller 40 comprises control circuitry 42, which is electrically connected to electrodes 38 via longitudinal member 32. Controller 40 is used (e.g., by an operating physician) (i) to drive electrode 38a to apply an ablative current (i.e., to tissue adjacent to the electrode), and (ii) to drive electrode 38b to apply an excitatory current (i.e., to tissue adjacent to the electrode). The ablative and excitatory currents are therefore applied while catheter 30 and its electrodes remain in the same position. For some applications, the ablative and excitatory currents are applied generally at the same time. For some applications, the ablative and excitatory currents are applied independently of each other. A response of one or more physiological parameters to the excitatory current is measured.

Controller 40 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Such program code and/or data, when provided to the controller, produce a machine or special-purpose computer, configured to perform the tasks described herein. Controller 40 further comprises a user interface (UI) 46 via which the operating physician interacts with (e.g., operates) the controller. For example, UI 46 may comprise one or more input devices (e.g., buttons and/or levers) and/or one or more output devices (e.g., dials and/or displays). For some applications, controller 40 is electrically connected to a blood pressure sensor (which may be disposed on longitudinal member 32; not shown), and receives blood pressure measurements, thereby facilitating the identification and/or quantification of the response of the one or more physiological parameters to the excitatory current.

Longitudinal member 32 is subsequently moved distally such that electrode 38b moves toward the starting position 12 of electrode 38a, and stops there (FIG. 1B). As shown, this also causes electrode 38a to move into a new position 14, electrode 38c to move into the starting position of electrode 38b, and electrode 38d to move into the starting position of electrode 38d. In this position, controller 40 is again used (i) to drive electrode 38a to apply an ablative current, and (ii) to drive electrode 38b to apply an excitatory current, and again, a response of one or more physiological parameters to the excitatory current is measured. As described hereinabove, the ablative and excitatory currents are applied while catheter 30 and its electrodes remain in the same position (and optionally generally at the same time). This reduces the number of steps (and therefore time) required, compared to a similar procedure in which it is necessary to move the electrode catheter between each application of current.

Figure 1C:
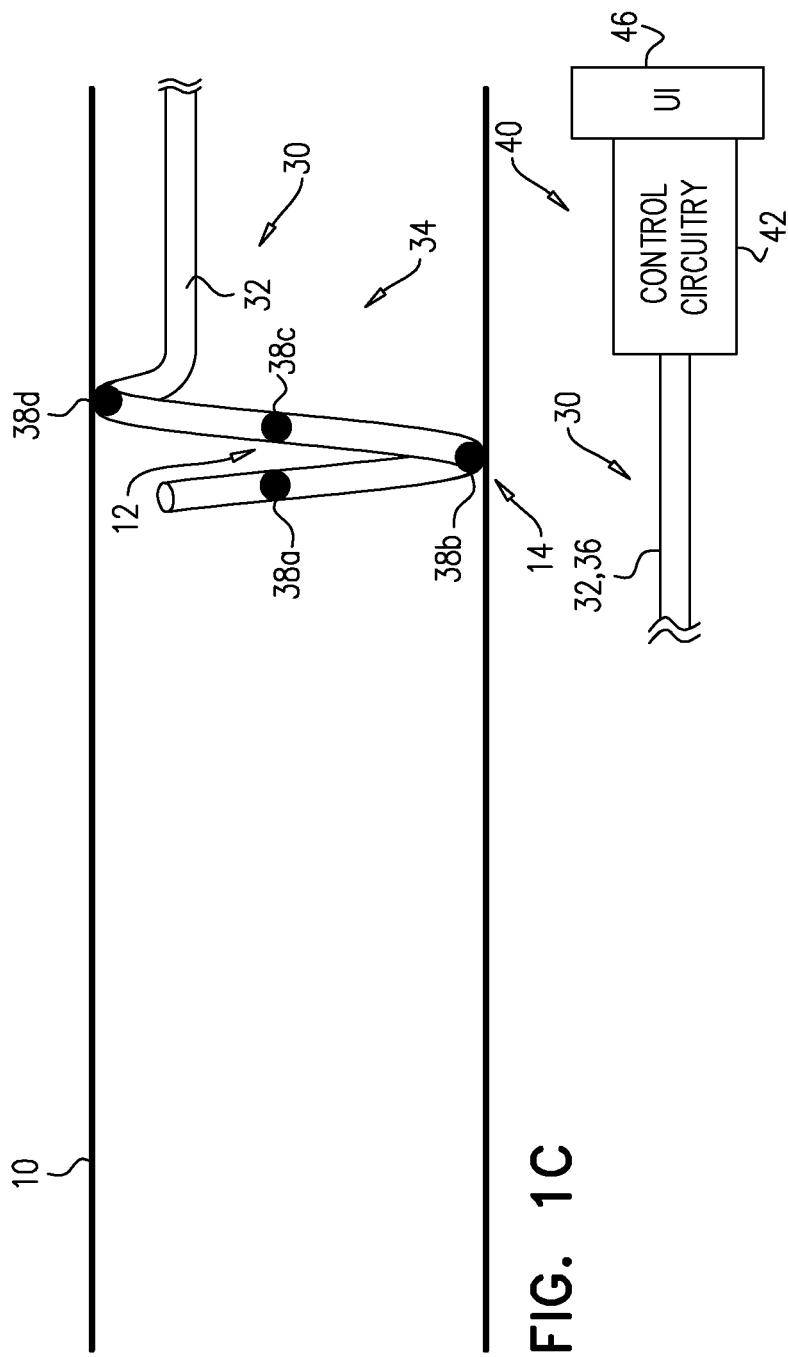

FIGS. 1C and 1D show further iterative steps in this process.

For some applications, the movement of longitudinal member 32 distally is performed manually. For some such applications, the longitudinal member (e.g., proximal portion 36 thereof) has markers that are spaced according to the spacing of electrodes 38, such that the operating physician can advance the longitudinal member by one marker, knowing that this will place each electrode in the position that was previously occupied by another electrode. For some applications (e.g., as described hereinbelow with reference to FIGS. 2A-B) the movement of longitudinal member 32 distally is at least partly automated.

For some applications, and as shown, distal portion 34 of longitudinal member 32 has an operational shape in which it is curved to define a helix, and electrodes 38, which are distributed along distal portion 34, are thereby distributed in a helical arrangement. This is hypothesized to facilitate ablation at many circumferential positions around artery 10, but without ablating in a closed circle, which for some applications may cause narrowing and/or weakening of the artery. For such applications, the step of moving the longitudinal member 32 distally comprises moving the longitudinal member distally and rotating at least distal portion 34 such that electrode 38b moves (e.g., in a helical path) toward the starting position of electrode 38a, and stops there.

For some applications, the step of moving longitudinal member 32 distally comprises moving the longitudinal member distally without rotating distal portion 34. For some such applications, distal portion 34 may be helical, as shown. Alternatively, for some such applications distal portion 34 may have a different form, such as a basket or balloon.

The above description of the method shown in FIGS. 1A-D relates to two electrodes. As described hereinabove, catheter 30 may comprise a different number of electrodes (e.g., four electrodes, as shown). The method described with reference to FIGS. 1A-D is also applicable to such numbers of electrodes. Two such applications are as follows:

(1) More proximal electrodes may be used to repeat the ablation-excitation process at a given site on artery 10. For example, if it is determined that the physiological parameter responds to the excitatory current applied by electrode 38b to starting position 12 (FIG. 1B), another application of ablative current may be applied via electrode 38c when it is disposed at position 12 (FIG. 1C), and another application of excitatory current may be subsequently applied via electrode 38d when that electrode is disposed at position 12 (FIG. 1D).

(2) More than one electrode may be used to apply a current. That is, application of the ablative and/or excitatory current may be performed in a bipolar manner. For example, ablative current may be applied between electrodes 38a and 38c, and excitatory current may be applied between electrodes 38b and 38d.

For some applications, the ablative current has a frequency of 450-550 kHz and/or a power of 1-7 W. For some applications, the ablative current has a sinusoidal waveform.

For some applications, the excitatory current has a frequency of 20-500 Hz and/or a stimulation amplitude of 1-50 mA. For some applications, the excitatory current has a rectangular waveform.

Reference is now made to FIGS. 2A-B, which are schematic illustrations of a system 20 for use with artery 10 of a subject, in accordance with some applications of the invention. System 20 comprises electrode catheter 30 and a controller 60 for the electrode catheter. Controller 60 is typically as described for controller 40, except where noted. System 20 is typically used to facilitate the method described with reference to FIGS. 1A-D, and/or methods similar thereto.

Controller 60 comprises control circuitry 62, which is electrically connected to electrodes 38 via longitudinal member 32. Controller 60 also comprises a user interface (UI) 66, via which the operating physician interacts with the controller. Controller 60 further comprises an actuator 64, which is mechanically connected to longitudinal member 32, and is configured to move the longitudinal member in discrete incremental movements such that for each incremental movement, (a) before the incremental movement the first electrode is disposed in a starting position, (b) during each incremental movement the actuator moves second electrode toward the starting position of the first electrode, and (c) at the end of each incremental movement the second electrode is stationary at the starting position of the first electrode.

In order to perform the movements of catheter 30 described with reference to FIGS. 1A-D, the operating physician triggers actuator 64 (e.g., via UI 66) such that the actuator moves longitudinal member 32 the discrete increment (e.g., distally, or distally and rotationally). The arrows in FIG. 2B show the movement of longitudinal member 32 and electrodes 38 during the discrete incremental movement that will occur when the operating physician next triggers actuator 64. Each incremental movement is typically predetermined, e.g., based on known dimensions of longitudinal member 32 and spacing of electrodes 38. For some applications, actuator 64 comprises a servomotor. The use of controller 60 to automatically move the longitudinal member such that each electrode moves into the position that the electrode distal to it previously occupied, reduces the requirement for imaging (e.g., fluoroscopy) during the procedure.

The applications of ablative and excitatory currents are also typically applied by the operating physician via UI 66.

Reference is again made to FIGS. 1A-2B. For some applications, the electrodes are differently configured for application of ablative or excitatory currents. For some applications, all the electrodes are identical other than in their respective connection to the controller, which differentially drives the electrodes to apply the respective type of current.

Catheter 30 is described as having its distalmost electrode (electrode 38a) apply ablative current, and for the electrode proximal to that (electrode 38b) apply excitatory current. However, for some applications, the distalmost electrode applies excitatory current, and the electrode proximal to that applies ablative current. For example, the controller may drive electrode 38a to apply excitatory current, electrode 38b to apply ablative current, electrode 38c to apply excitatory current, and so on. For such applications, each site in artery 10 is thereby tested (by applying excitatory current and measuring the physiological response) before any ablative current is applied to it, thereby reducing the number of unnecessary applications of ablative current. An exemplary procedure may be as follows:

(1) Distal portion 34 of longitudinal member 32 is advanced into artery 10, electrode 38a is driven to apply excitatory current. If the physiological response to the excitatory current is insufficient or absent, the catheter is repositioned (e.g., advanced distally) and excitatory current is reapplied via electrode 38a, iteratively until a sufficient physiological response is detected, indicating that electrode 38a is in proximity to a viable renal nerve. For this example, let the position of electrode 38a in which it successfully excited the nerve, be called position A.

(2) Distal portion 34 is advanced distally such that electrode 38b moves to and stops at position A, and electrode 38a moves to and stops at a new position B.

(3) Electrode 38a is driven to apply excitatory current at position B, and electrode 38b is driven to apply ablative current at position A. Typically, distal portion 34 is not moved between the application of these two currents. For some applications, these two currents are applied at generally the same time. Therefore, electrode 38a tests position B, and electrode 38b ablates at position A, without it being necessary to move catheter 30 between these functions being performed.

(4) Distal portion 34 is advanced distally, such that electrode 38a moves to a new position C, electrode 38b moves to position B, and electrode 38c moves to position A.

(5) Electrode 38a is driven to apply excitatory current at position C, and electrode 38c is driven to apply excitatory current at position A. Additionally, if the previous excitation by electrode 38a at position B successfully affected the physiological parameter, then electrode 38b is driven to apply ablative current at position B. Typically, distal portion 34 is not moved between the application of these two or three currents. For some applications, these two or three currents are applied at generally the same time. Therefore, electrode 38a tests position C, electrode 38c re-tests position A (to see if the ablative current successfully denervated that location), and optionally electrode 38b ablates at position B, without it being necessary to move catheter 30 between these functions being performed.

These steps are iteratively repeated along the artery, e.g., to positions D, E, F, G, and so on. For applications in which another electrode, disposed proximally from electrode 38c, is configured to apply ablative current (e.g., electrode 38d), if the re-testing of position A by electrode 38c determines that the first ablation of position A by electrode 38a was unsuccessful, then this other electrode may be used to re-apply ablative current at position A. Increasing the number of ablating and exciting electrodes along distal portion 34 allows an increased number of re-testing and re-ablating steps using this technique.

Figure 3C:
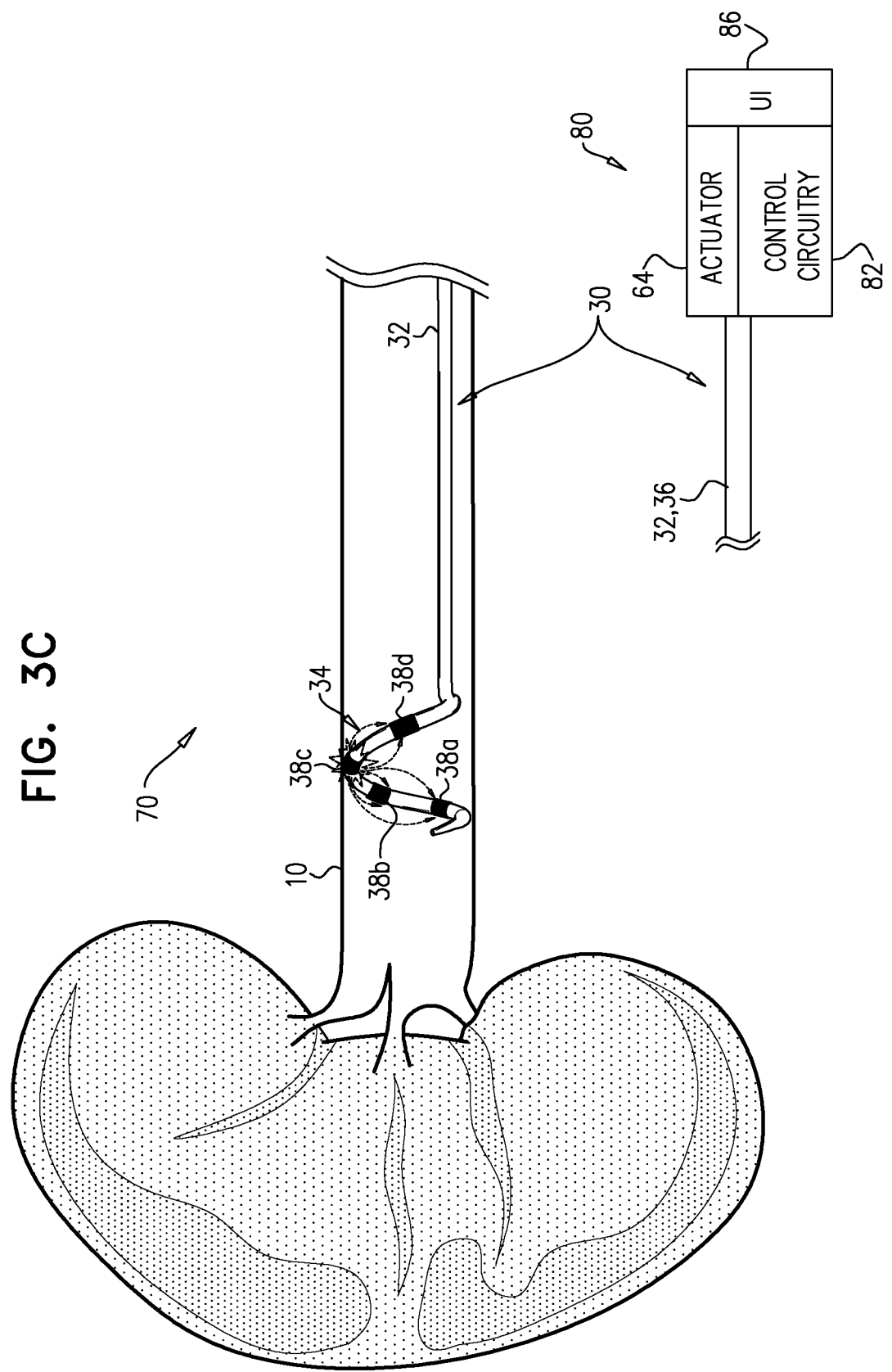

Reference is made to FIGS. 3A-C, which are schematic illustrations of a system 70 for use with artery 10 of a subject, in accordance with some applications of the invention. System 70 comprises electrode catheter 30 and a controller 80 for the electrode catheter. Alternatively, system 70 may comprise a different electrode catheter. Controller 80 is typically as described for controller 60, except where noted. Controller 80 comprises control circuitry 82, which is electrically connected to electrodes 38 via longitudinal member 32. Controller 80 also comprises a UI 86, via which the operating physician interacts with the controller. Controller 80 may or may not comprise actuator 64 (described hereinabove).

Controller 80 has a first state in which it drives one of electrodes 38 to apply ablative current, and configures the other electrodes not to serve as return electrodes for the ablative current. (It is to be noted that in this context the terms first state, second state, third state etc. are used to facilitate reference to the different states, and should not be understood as implying a particular order in which these states occur or are used). FIG. 3A shows system 70 with controller 80 in the first state, driving electrode 38b to apply ablative current, with electrodes 38a, 38c, and 38d not serving as return electrodes. In the first state, a skin-mounted return electrode is typically used. The ablative current is represented by dotted arrows, moving deeper into the surrounding tissue, e.g., toward the skin-mounted return electrode. This is typically referred to as monopolar ablation.

It is understood by the inventors that for some sites within a particular renal artery, monopolar ablation is preferable, and for some sites, bipolar ablation is preferable. For some applications, this is determined during the excitation steps described hereinabove, and/or during procedures described in the patent applications cited hereinabove, and incorporated herein by reference.

Controller 80 has a second state in which it drives one of electrodes 38 to apply ablative current, and configures more than one of the other electrodes to serve as return electrodes for the ablative current. FIG. 3B shows system 70 with controller 80 in the second state, driving electrode 38b to apply ablative current, with electrodes 38a, 38c, and 38d serving as return electrodes. The ablative current is represented by dotted arrows, moving from electrode 38b toward the three return electrodes. In classical bipolar ablation, ablative current is driven between two electrodes, and current-density at the return electrode is typically similar to that at the current-applying electrode. Frequently, the resulting lesion may extend between the two electrodes, or a separate lesion may be formed at the return electrode. In the second state of controller 80, the current applied by the current-applying electrode (electrode 38b) spreads toward the more-than-one return electrodes, such that the current-density at each of the return electrodes is lower than at the current-applying electrode. It is hypothesized by the inventors that the effect of this technique is similar to that of monopolar ablation, but advantageously doesn't require a skin-mounted electrode. Control and reliability are improved because the distance and tissue between the current-applying electrode and the return electrodes is less variable than with a skin-mounted return electrode. Additionally, in contrast to bipolar ablation, the spreading of current to more than one return electrodes reduces a likelihood of causing extended and/or secondary lesions.

For some applications, the same electrode (as shown, electrode 38b) is driven to apply the ablative current in both the first and second states.

For some applications, controller 80 has a third state in which it drives one of electrodes 38 to apply ablative current, and configures more than one of the other electrodes to serve as return electrodes for the ablative current. One of the electrodes that serves as a return electrode in the third state is the electrode that in the second state controller 80 drives to apply ablative current. FIG. 3C shows system 70 with controller 80 in the third state, driving electrode 38c to apply ablative current, with electrode 38b serving as one of the return electrodes.

For some applications, controller 80 has another state in which only one of the other electrodes serves as a return electrode, thereby performing classical bipolar ablation.

Although the techniques described with reference to FIGS. 3A-C refer to application of ablative current, these same techniques may be used for application of excitatory current, mutatis mutandis.

Reference is again made to FIGS. 1A-3C. Although the apparatus and methods described herein are described for iteratively moving distal portion 34 in a distal direction (e.g., from an ostium of renal artery 10 toward a kidney), they may alternatively be used by moving the distal portion in a proximal direction, mutatis mutandis.

Reference is again made to FIGS. 1A-3C. Although not shown, distal portion 34 is typically drawn toward its central longitudinal axis (and thereby away from the wall of artery 10) before each movement being moved distally (or proximally) through the artery. For example, when distal portion 34 is helical, this is typically achieved by straightening the helix. For some applications, distal portion 34 is biased to assume a relatively straight shape, and assumes its helical shape upon insertion of a pre-shaped rod into the distal portion.

Reference is again made to FIGS. 1A-3C. For some applications electrodes 38 are rings that circumscribe longitudinal member 32. For some applications, electrodes 38 do not circumscribe longitudinal member 32, and instead are disposed on the longitudinal member such that when distal portion 34 assumes the helical shape, they are disposed radially outward from the longitudinal member such that they face the wall of the blood vessel.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a blood vessel of a subject, the apparatus comprising:
    a longitudinal member, having a distal portion that is transluminally advanceable into the blood vessel;
    a plurality of electrodes disposed on the distal portion of the longitudinal member, such that a first electrode of the plurality of electrodes is disposed distally along the longitudinal member from a second electrode of the plurality of electrodes, wherein the distal portion of the longitudinal member has an operational shape in which it is curved to define a helix, the plurality of electrodes is distributed in a helical arrangement along the distal portion of the longitudinal member; and
    a controller, comprising:
    circuitry electrically connected to the electrodes via the longitudinal member, and
    an actuator, mechanically connected to the longitudinal member, and configured to move the longitudinal member in discrete incremental movements distally and rotationally such that for each incremental movement, (a) before the incremental movement the first electrode is disposed in a starting position, (b) during each incremental movement the actuator moves second electrode toward the starting position of the first electrode, and (c) at the end of each incremental movement the second electrode is stationary at a location that is both longitudinally and laterally the same as the starting position of the first electrode;

wherein the circuitry is configured to drive the first electrode to apply ablative current, and to drive the second electrode to apply excitatory current.

2. The apparatus according to claim 1, wherein:
the plurality of electrodes comprises a third electrode and a fourth electrode,
the third electrode is disposed distally along the longitudinal member from the fourth electrode, and
the actuator is configured to move the longitudinal member in incremental movements such that for each incremental movement, (a) before the incremental movement the third electrode is disposed in a starting position, (b) during each incremental movement the actuator moves fourth electrode toward the starting position of the third electrode, and (c) at the end of each incremental movement the fourth electrode is stationary at the starting position of the third electrode.

3. The apparatus according to claim 1, wherein:
the plurality of electrodes comprises a third electrode and a fourth electrode,
the third electrode is disposed distally along the longitudinal member from the fourth electrode, and
the actuator is configured to move the longitudinal member in incremental movements such that for each incremental movement, (a) before the incremental movement the third electrode is disposed in a starting position, (b) during each incremental movement the actuator moves fourth electrode toward the starting position of the third electrode, and (c) at the end of each incremental movement the fourth electrode is stationary at the starting position of the third electrode,
wherein the circuitry is configured to, after each incremental movement, drive the first and third electrodes to apply ablative current, and to drive the second and fourth electrodes to apply excitatory current.

4. The apparatus according to claim 1, wherein the actuator comprises a servomotor.

5. The apparatus according to claim 1, wherein the circuitry is configured to drive the first electrode to apply ablative current, and to drive the second electrode to apply excitatory current after each incremental movement.

6. The apparatus according to claim 1, wherein the circuitry is configured to configure the ablative current to have a frequency of 450-550 kHz.

7. The apparatus according to claim 1, wherein the circuitry is configured to configure the excitatory current to have a frequency of 20-500 Hz.

8. The apparatus according to claim 1, wherein the circuitry is configured to drive the first electrode to apply the ablative current independently from driving the excitatory current.

9. A method for using the apparatus of claim 1, comprising:
advancing into a blood vessel of a subject the distal portion of the longitudinal member having the plurality of electrodes disposed thereon, such that the first electrode of the plurality of electrodes is disposed at the starting position, the first electrode being disposed, along the distal portion, distally to the second electrode of the plurality of electrodes;
using the controller to drive the first electrode to apply an ablative current;
using the controller to drive the second electrode to apply an excitatory current; and
subsequently, moving the longitudinal member distally and rotating at least the distal portion of the longitudinal member such that the second electrode moves toward the starting position of the first electrode, and stops at the starting position of the first electrode.

10. The method according to claim 9, further comprising, subsequently to the step of moving the longitudinal member:
using the controller to drive the first electrode to apply an ablative current to tissue distal to the starting position of the first electrode; and
using the controller to drive the second electrode to apply an excitatory current to tissue at the starting position of the first electrode.

* * * * *

UNITED STATES PATENT AND TRADEMARK OFFICE
CERTIFICATE OF CORRECTION

PATENT NO. : 11,678,932 B2
APPLICATION NO. : 16/302150
DATED : June 20, 2023
INVENTOR(S) : Gross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this
Nineteenth Day of November, 2024

*Katherine Kelly Vidal*
Katherine Kelly Vidal
*Director of the United States Patent and Trademark Office*